United States Patent [19]
Grant et al.

[11] Patent Number: 5,312,024
[45] Date of Patent: May 17, 1994

[54] SURGICAL ANASTOMOSIS STAPLING INSTRUMENT WITH FLEXIBLE SUPPORT SHAFT AND ANVIL ADJUSTING MECHANISM

[75] Inventors: Richard L. Grant, Cincinnati, Ohio; Michael Lang, North Andover, Mass.; Philip J. Churchill, North Potomac, Md.; W. Thompson Lawrence, Lexington, Mass.

[73] Assignee: Ethicon, Inc., Somerville, N.J.

[21] Appl. No.: 71,280

[22] Filed: Jun. 2, 1993

Related U.S. Application Data

[62] Division of Ser. No. 832,299, Feb. 7, 1992, Pat. No. 5,271,543.

[51] Int. Cl.⁵ ............................................. A61B 17/115
[52] U.S. Cl. ........................................ 227/179; 227/19
[58] Field of Search .................. 227/19, 176, 177, 178, 227/179, 180

[56] References Cited

U.S. PATENT DOCUMENTS

| | | | |
|---|---|---|---|
| 3,193,165 | 7/1965 | Akhalaya et al. | 227/8 |
| 4,473,077 | 9/1984 | Noiles et al. | 128/305 |
| 4,485,817 | 12/1984 | Swiggett | 128/334 R |
| 4,488,523 | 12/1984 | Shichman | 128/334 R |
| 4,576,167 | 3/1986 | Noiles | 128/334 R |
| 4,606,343 | 8/1986 | Conta et al. | 128/305 |
| 4,646,745 | 3/1987 | Noiles | 128/334 R |
| 4,671,445 | 6/1987 | Barker et al. | 227/19 |
| 4,754,909 | 7/1988 | Barker et al. | 227/19 |
| 4,907,591 | 3/1990 | Vasconcellos et al. | 227/19 X |
| 4,962,877 | 10/1990 | Hervas | 227/179 |
| 5,005,749 | 4/1991 | Aranyi | 227/179 |
| 5,042,707 | 8/1991 | Taheri | 227/179 X |
| 5,104,025 | 4/1992 | Main et al. | 227/175 |
| 5,139,513 | 8/1992 | Segato | 606/219 |
| 5,205,459 | 4/1993 | Brinkerhoff et al. | 227/19 X |

FOREIGN PATENT DOCUMENTS

| | | | |
|---|---|---|---|
| 3300768 | 4/1985 | Fed. Rep. of Germany | A61B 17/11 |
| 83/02247 | 7/1983 | PCT Int'l Appl. | 227/19 |
| 85/01428 | 4/1985 | PCT Int'l Appl. | 227/19 |

Primary Examiner—Rinaldi I. Rada
Attorney, Agent, or Firm—Paul A. Coletti

[57] ABSTRACT

A surgical stapling instrument for performing a circular anastomosis stapling operation is provided. The surgical instrument includes a stapling head assembly mounted by a flexible support shaft to an actuator handle assembly. The support shaft is capable of bending in any radial direction relative to its centerline into a curved configuration suitable for insertion into a patient. The flexible support shaft includes a dual coil structure which is adapted to support itself in any curved configuration and to resist deflection upon insertion into the patient and actuation of the stapling head assembly. The stapling head assembly includes a driver assembly which is operable in multiple stages to separate te staple forming and tissue cutting actions to reduce the peak force required to operate the instrument. The actuator handle assembly includes a staple actuating lever and a cam follower assembly which operate in two stages with different mechanical advantages to facilitate the operation of the instrument by a surgeon. The actuator handle assembly includes a thumb wheel for opening and closing the anvil and an adjusting knob for adjusting the anvil gap. A control lever is provided for pivoting the stapling head assembly relative to the flexible support shaft.

7 Claims, 18 Drawing Sheets

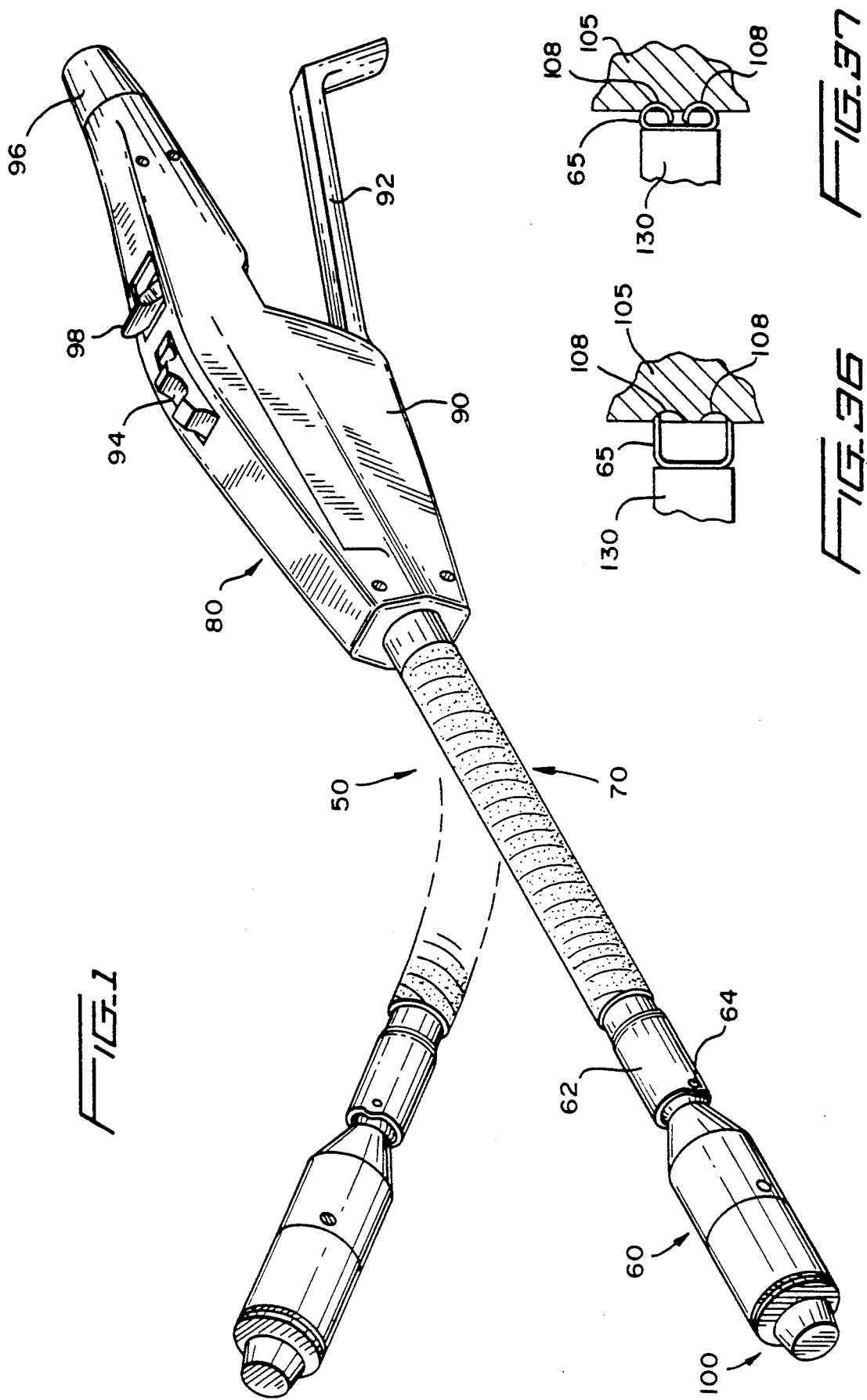

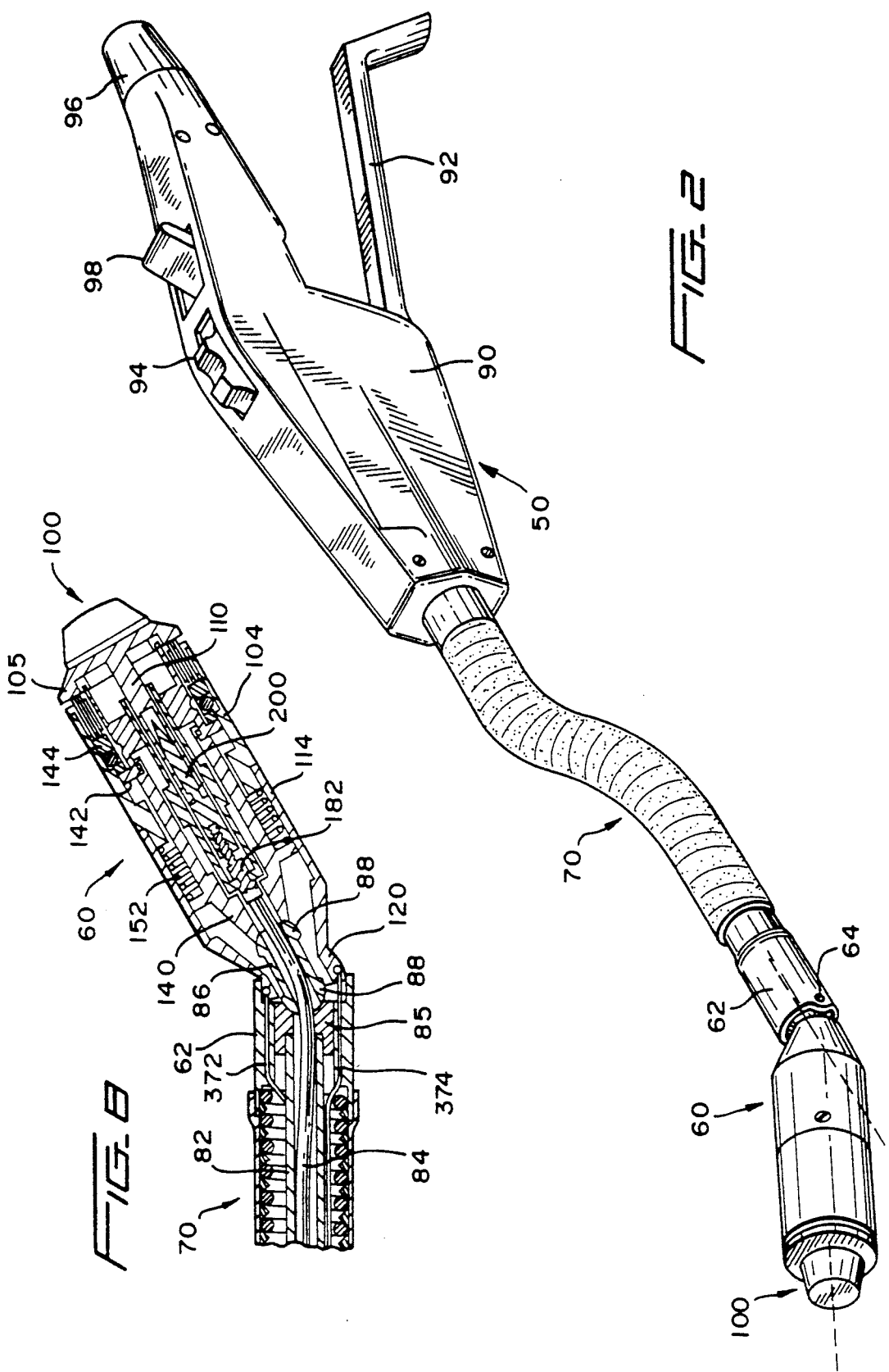

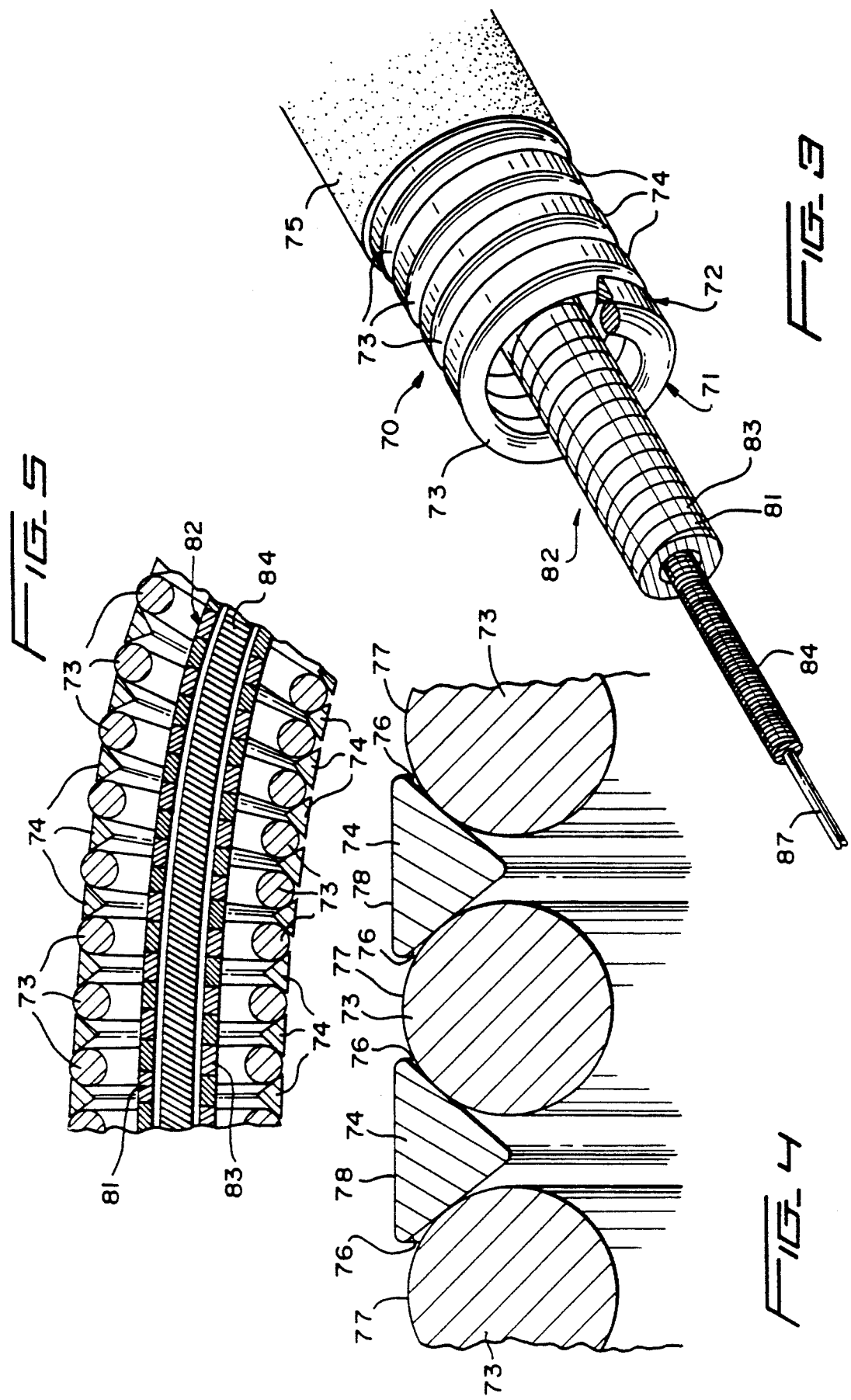

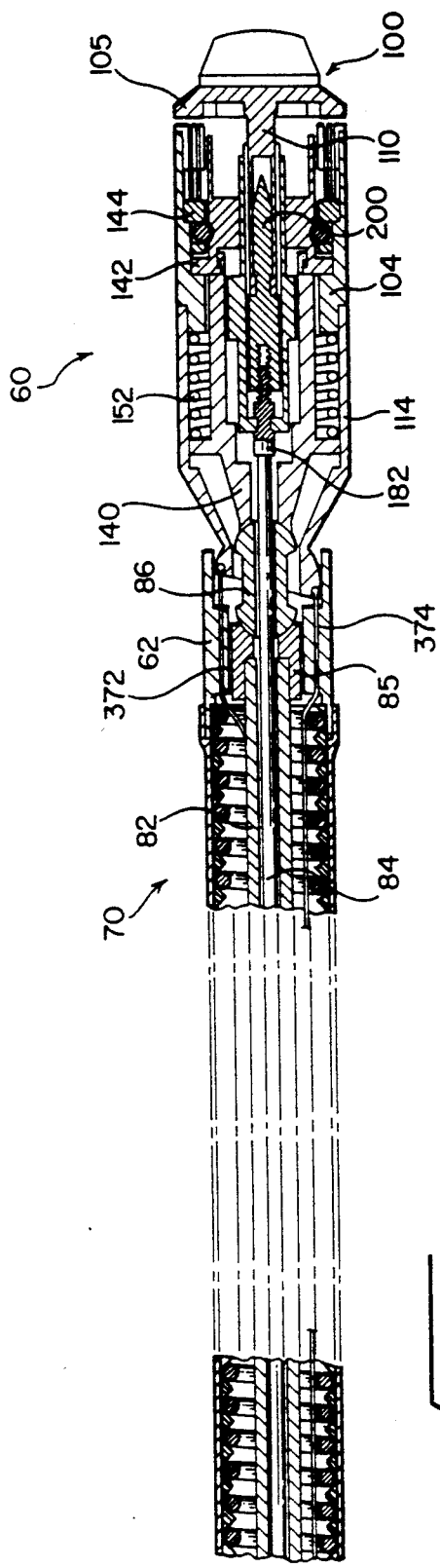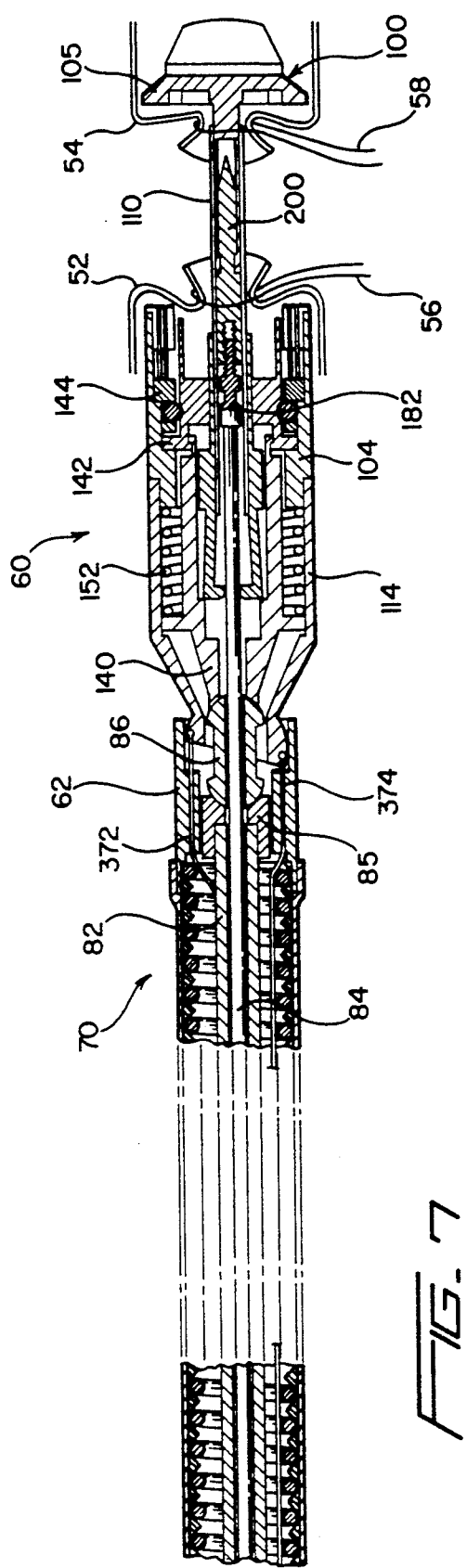

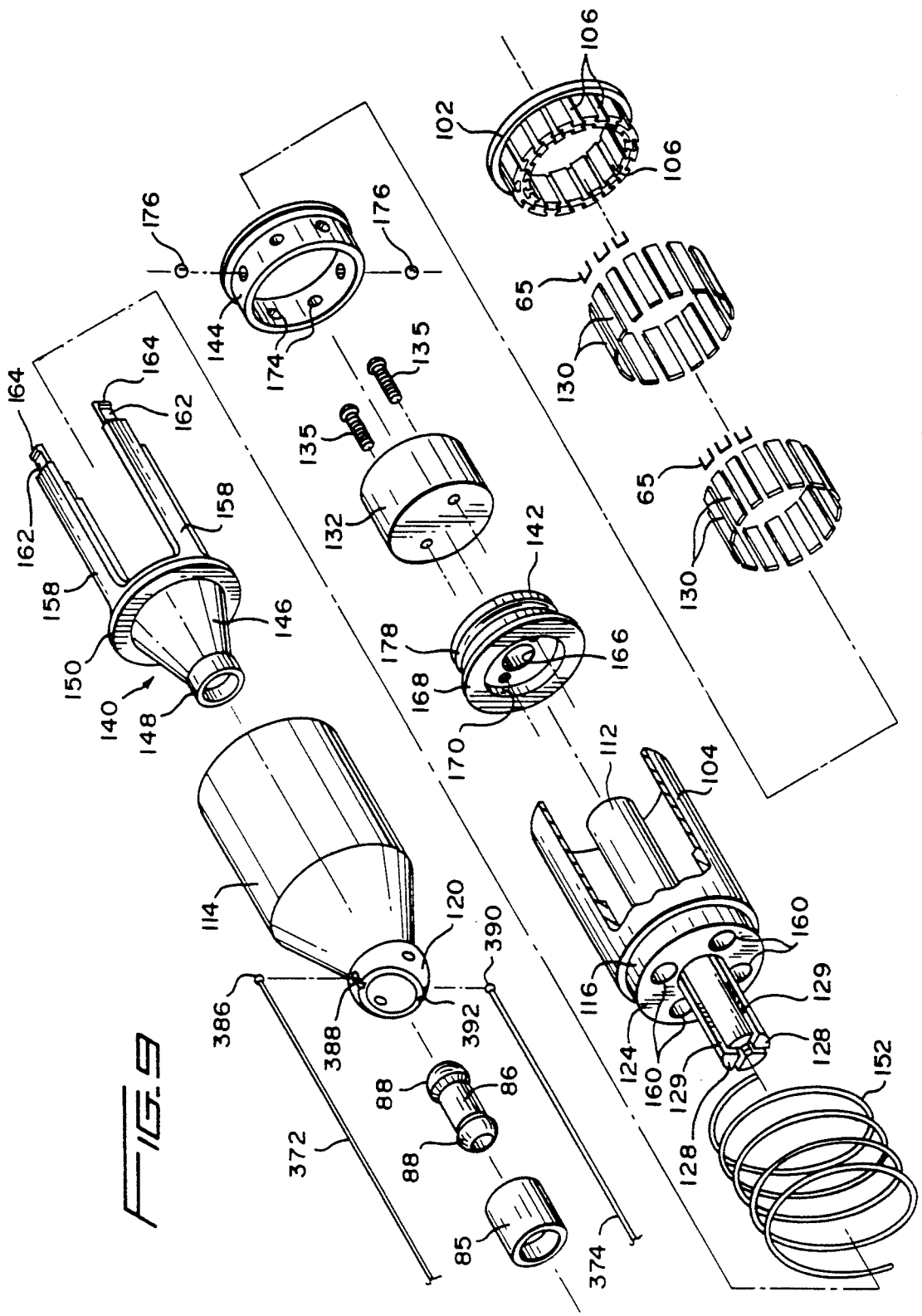

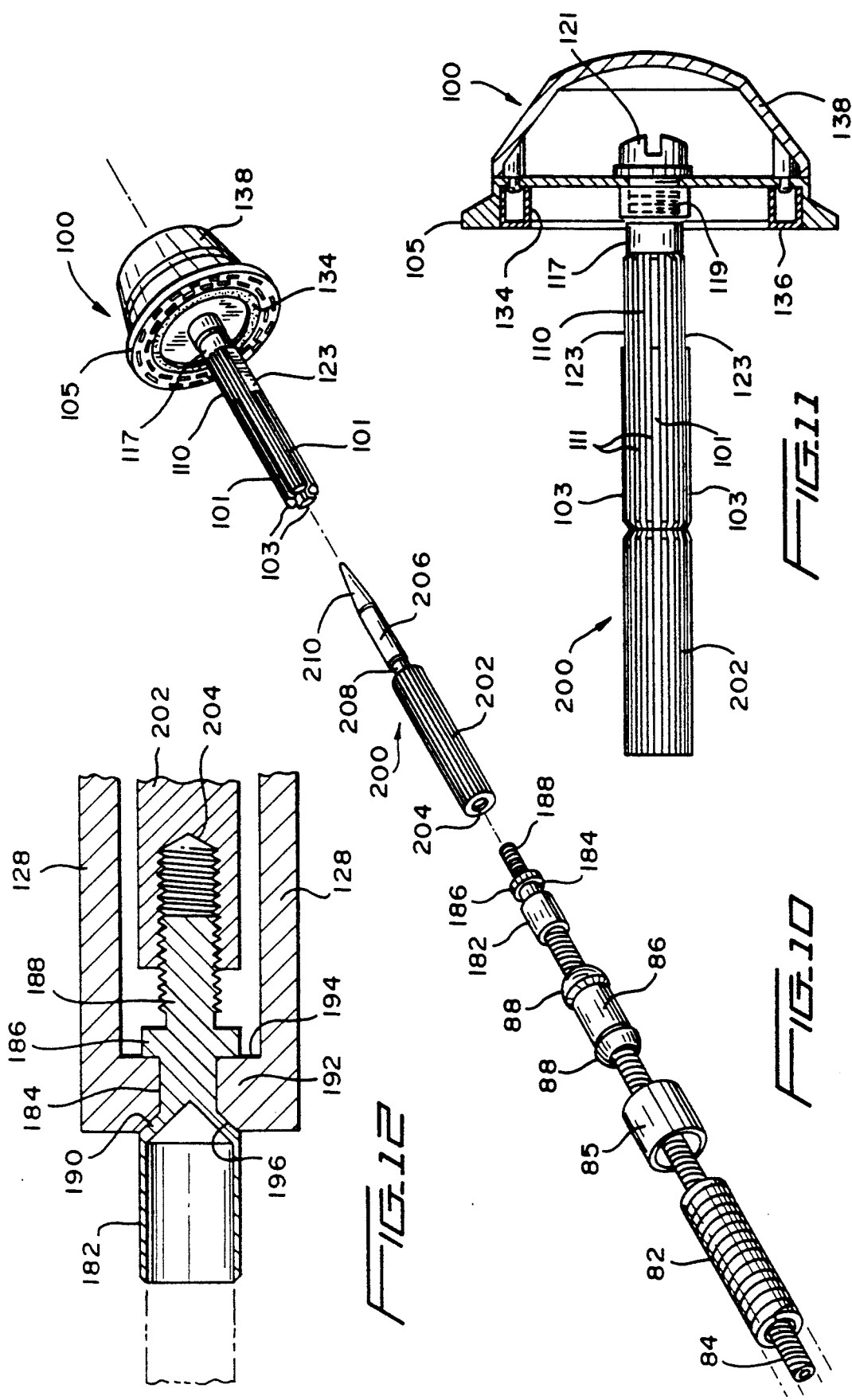

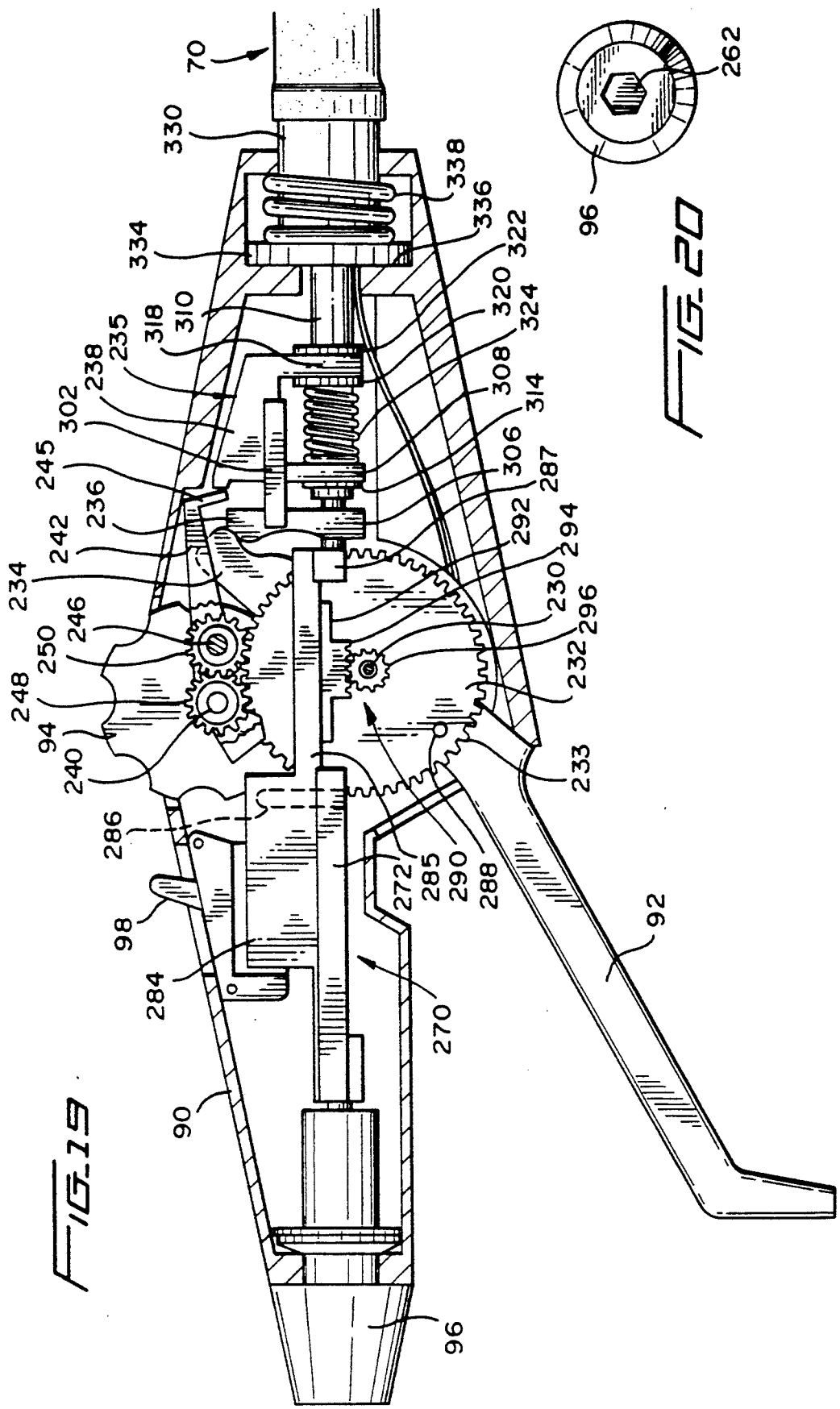

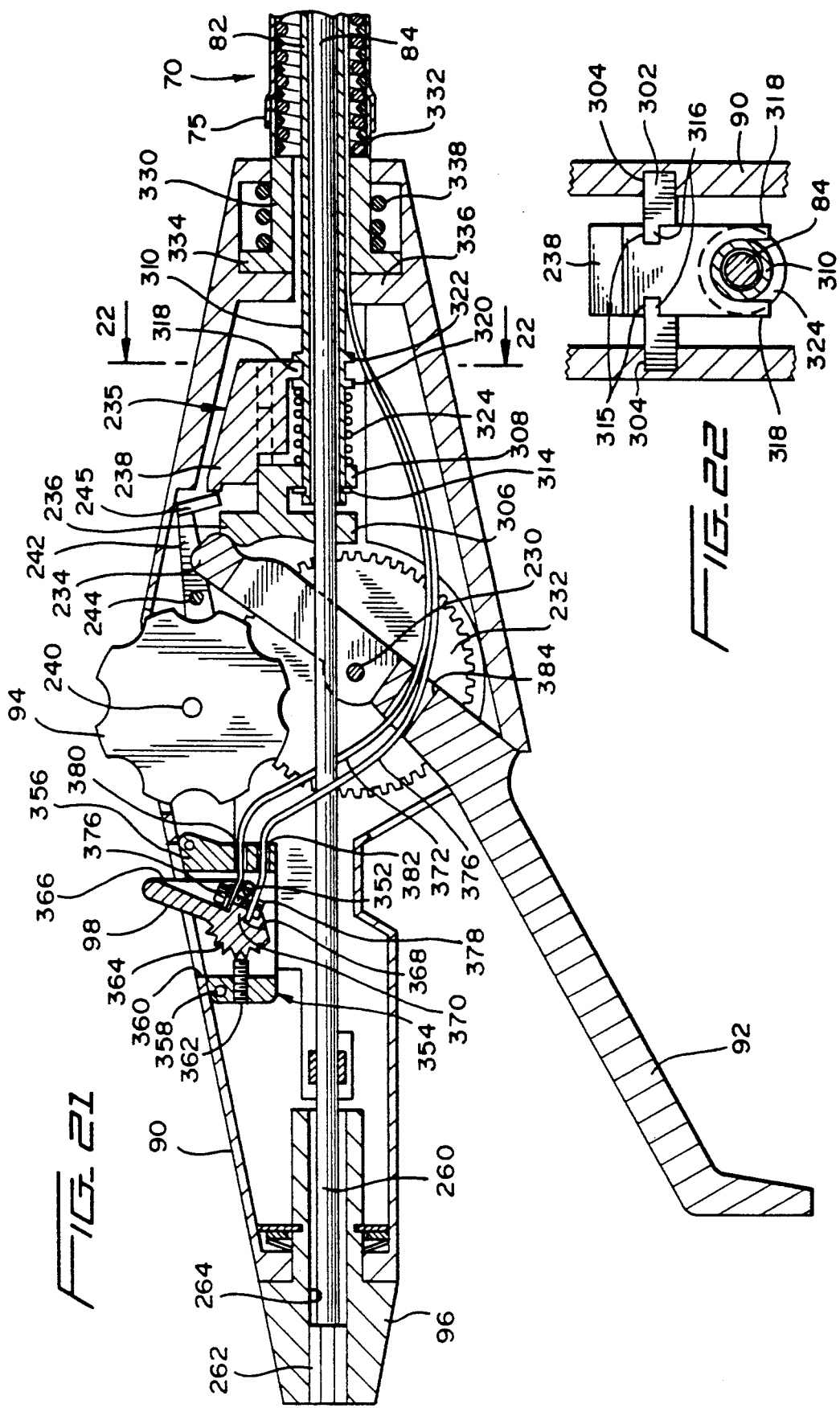

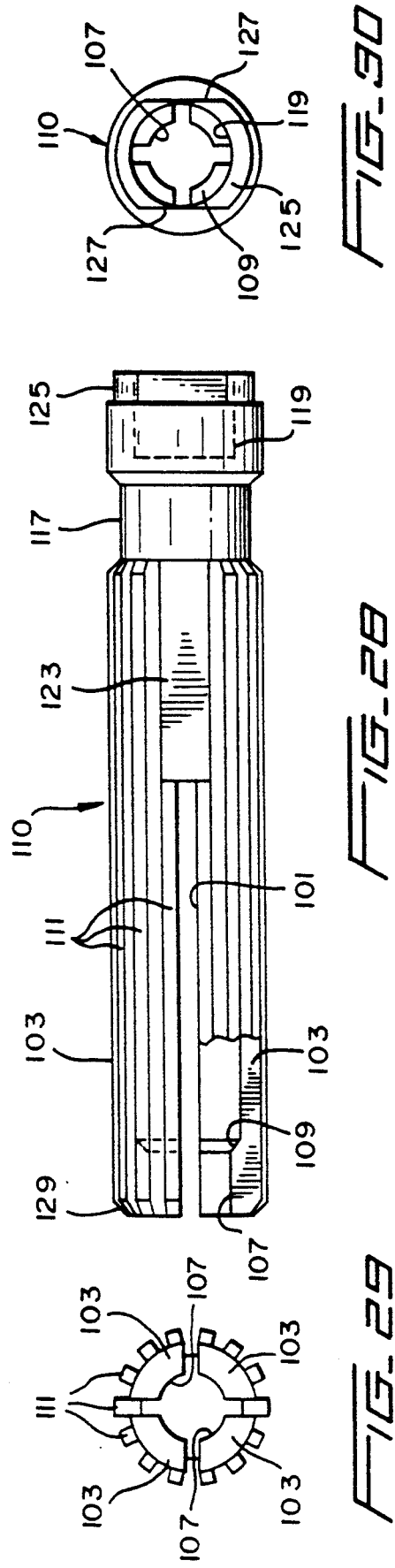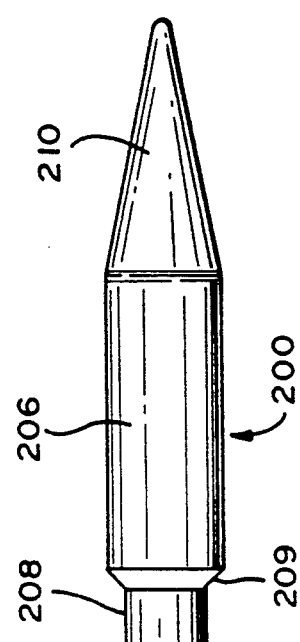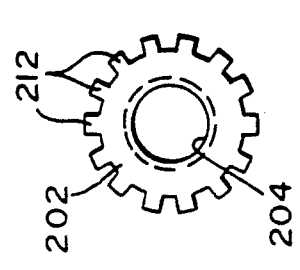

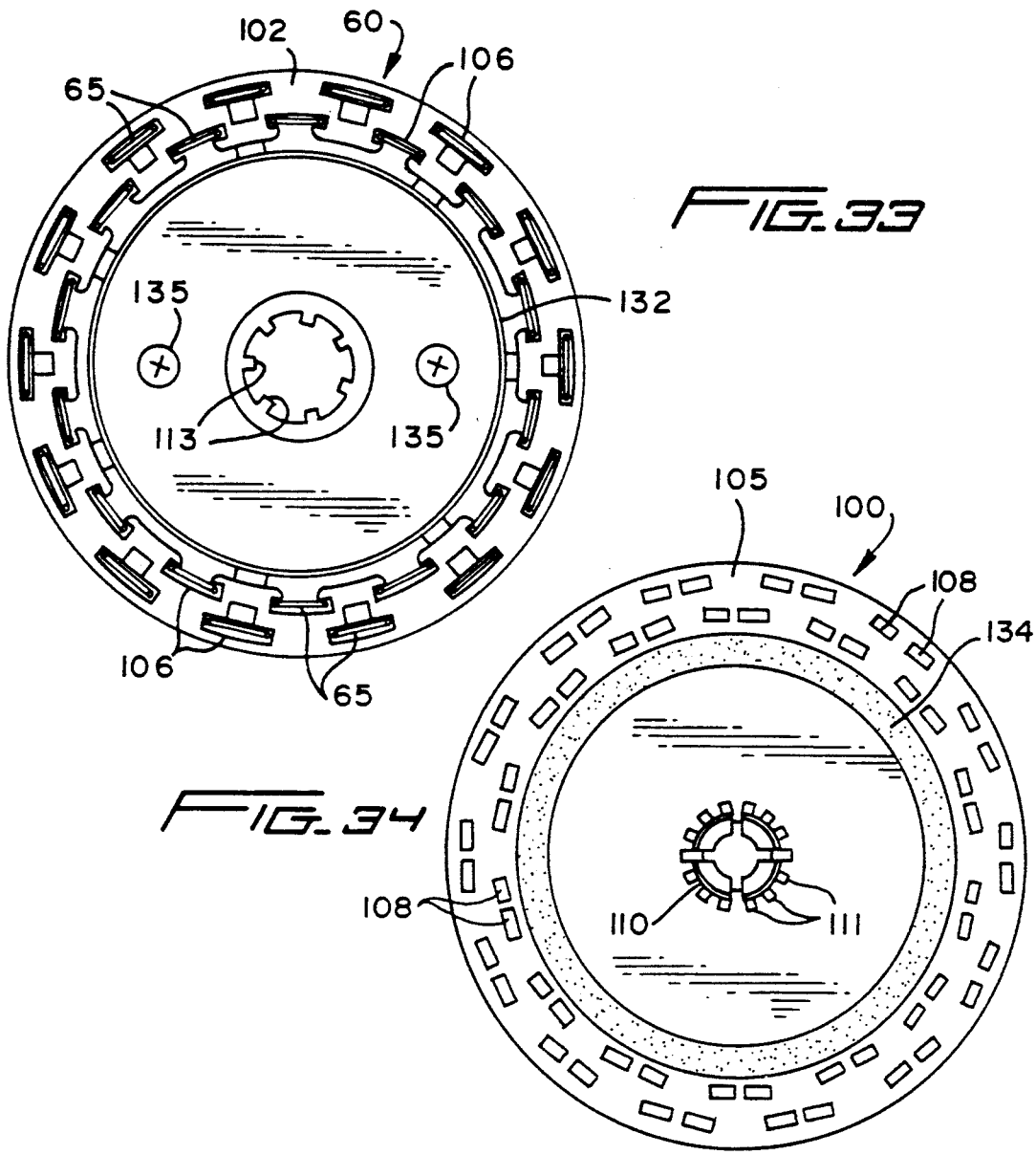
FIG. 33
FIG. 34
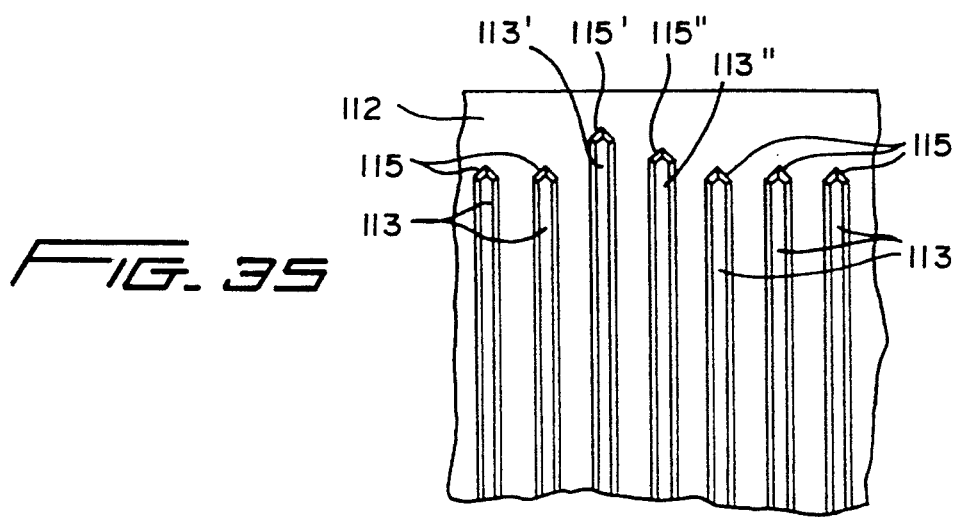
FIG. 35

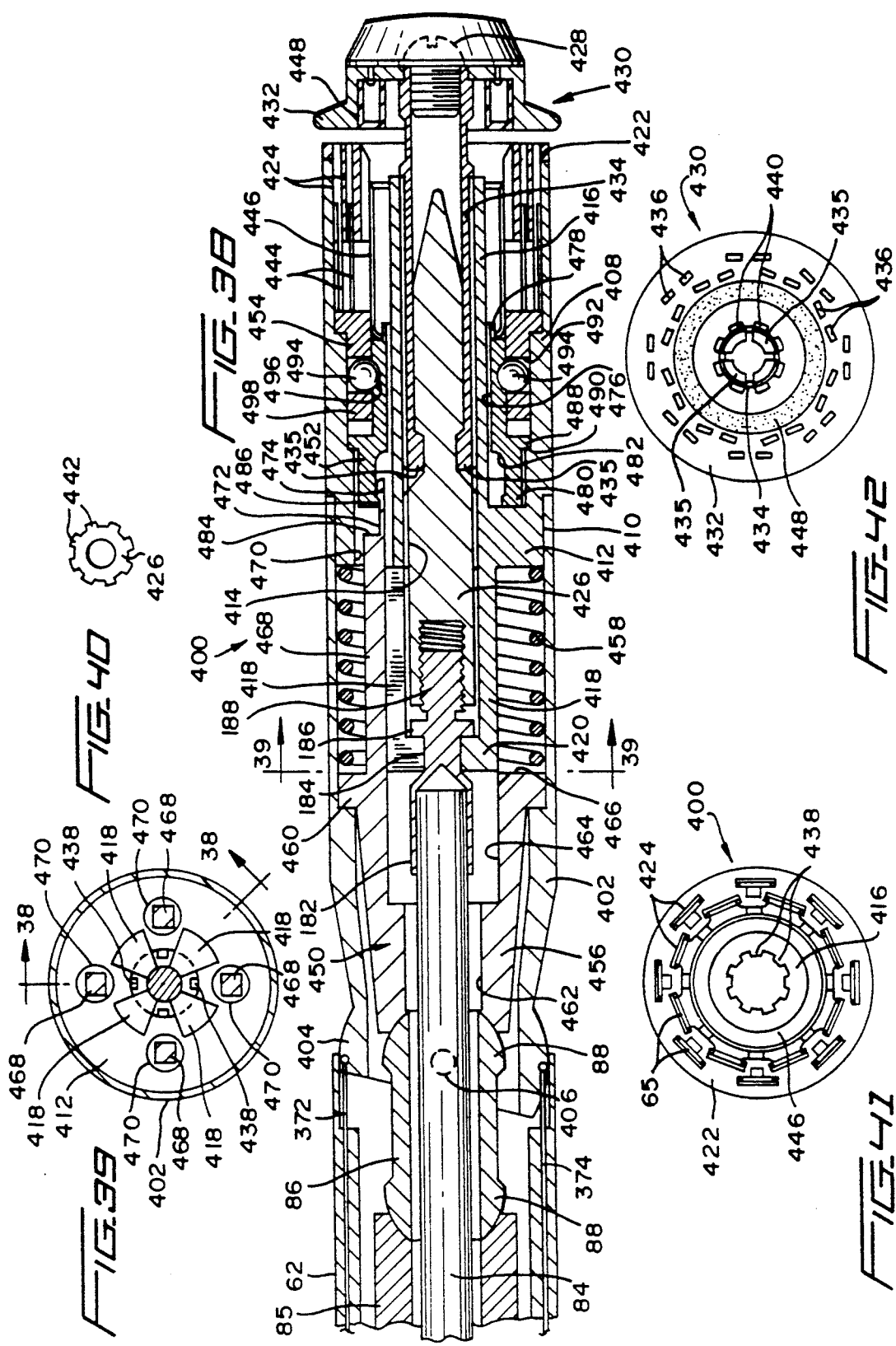

SURGICAL ANASTOMOSIS STAPLING INSTRUMENT WITH FLEXIBLE SUPPORT SHAFT AND ANVIL ADJUSTING MECHANISM

This is a division, of application Ser. No. 832,299, filed Feb. 7, 1992, now U.S. Pat. No. 5,271,543, which is hereby incorporated by reference.

BACKGROUND OF THE INVENTION

1. Field of the Invention

The present invention generally relates to a surgical stapling instrument for applying surgical staples to tissue and, more particularly, to a surgical stapling instrument for performing a circular anastomosis stapling operation. More specifically, this invention relates to a surgical instrument in which a stapling head assembly is mounted by a flexible shaft to an actuator handle assembly and to an improved actuator mechanism for transmitting the required operating forces and movements from the actuator handle assembly through the flexible shaft to the stapling head assembly. Also, this invention relates to an improved stapling head assembly which reduces the operating forces required to perform the tissue stapling and cutting operations. Further, this invention concerns an improved actuator mechanism which controls the opening and closing of the stapling head assembly and adjustment of the anvil gap to produce a desired staple height.

2. Description of the Prior Art

The field of surgical stapling has seen substantial advances in the past decades. Specifically, in the area of internal anastomotic stapling the advances have been quite dramatic. Devices such as the Proximate ™ ILS stapler, produced by the assignee of the present invention, Ethicon, Inc., Somerville, N.J., have enabled surgeons to perform operations and procedures which were heretofore perceived as difficult, if not impossible, with relative ease.

Generally, in the performance of a surgical anastomotic stapling operation, two pieces of lumen or tubular tissue, e.g., intestinal tissue, are attached together by a ring of staples. The two pieces of tubular tissue may be attached end to end or one piece of tubular tissue may be attached laterally around an opening formed in the side of another piece of tubular tissue. In performing the anastomosis with a stapling instrument, the two pieces of tubular tissue are clamped together between an anvil provided with a circular array of staple forming grooves and a staple holder provided with a plurality of staple receiving slots arranged in a circular array in which the staples are received. A staple pusher is advanced to drive the staples into the tissue and form the staples against the anvil. Also, a circular knife is advanced to cut the excess tissue clamped between the anvil and the staple holder. As a result, a donut-shaped section of tissue is severed from each lumen and remains on the anvil shaft. The tubular tissue joined by the circular ring of staples is unclamped by advancing the anvil shaft distally to move the anvil away from the staple holder. The stapling instrument is removed by pulling the anvil through the circular opening between the pieces of tubular tissue attached by the ring of staples.

In the prior art, several types of circular anastomosis stapling instruments are known. For example, U.S. Pat. Nos. 4,576,167 and 4,646,745 to Noiles disclose a surgical stapler in which a stapling assembly is connected by an elongated shaft assembly having a longitudinally curved section to an actuator assembly. The shaft assembly includes an articulated hollow tube and a flexible band inside the tube, which are coaxial with a curved section of a hollow support shaft, for transmitting the compression and tension forces required to operate the stapling assembly.

It is also known in the prior art to provide a circular anastomosis stapling instrument including a flexible shaft which allows the stapling head to assume various orientations relative to the actuator assembly. Examples of circular stapling instruments with flexible shafts are disclosed in Noiles et al U.S. Pat. No. 4,473,077, Barker et al U.S. Pat. Nos. 4,671,445 and 4,754,909, Shichman U.S. Pat. No. 4,488,523, Swiggett U.S. Pat. No. 4,485,817 and Hervas U.S. Pat. No. 4,962,877.

Noiles et al U.S. Pat. No. 4,473,077 discloses a surgical stapling instrument including a stapling assembly and an actuator assembly connected by a longitudinal shaft assembly with a longitudinally flexible section. The flexible shaft section comprises an inner tube assembly including a plurality of washer-shaped segments, an outer tube assembly comprising a plurality of washer-shaped segments, and an outer elastic sheath. Inside the inner tube assembly is an actuator band for transmitting tension from the actuator assembly to the stapling assembly. The washer-shaped segments of each tube assembly provide lines of contact with the adjacent segments which allow the segments to pivot with respect to each other as the shaft assembly is deformed into a curve. The design of washer-shaped segments limits the bending of the shaft assembly to motion in a single plane, i.e., bending up or down in a vertical plane.

Barker et al U.S. Pat. No. 4,671,445 discloses a flexible surgical stapler assembly including a staple firing head assembly and a handle actuator assembly connected together by a flexible spine. The spine consists of a series of spine segments each having a hemispherically-shaped concave recess which mates with a hemispherically-shaped forward surface of the adjacent spine segment. A cable extends longitudinally through the spine segments from the handle actuator assembly to the staple firing head assembly. The spine segments abut one another and extend between the handle actuator assembly and the stapling head assembly and translate a force which maintains that portion of the staple firing head assembly to which the forwardmost spine segment abuts in a fixed position relative to the cable.

Barker et al U.S. Pat. No. 4,754,909 discloses a flexible stapler including a plurality of rigid spine segments having opposed concave and convex surfaces. The spine segments are disposed in end to end relationship to form a spine structure for connecting an actuator assembly to a stapling head assembly. A flexible stiffening assembly extends through aligned openings in the spine segments. The stapler includes tension applying means having a disengaged position at which sufficient slack is provided in the stiffening assembly to afford flexing of the spine structure to orient the spine segments and thereby the head assembly at a desired orientation relative to the actuator assembly and an engaged position at which tension is applied to the stiffening assembly to compress the spine segments and rigidify the spine structure.

Shichman U.S. Pat. No. 4,488,523 discloses a surgical stapler apparatus comprising an applicator portion and an actuator portion connected by a transversely flexible shaft. The flexible shaft contains a hydraulic line for connecting fluid chambers in the applicator and actuator portions. The hydraulic line is shaped as a helix and housed in a cylindrical sheath of flexible material.

Swiggett U.S. Pat. No. 4,485,817 discloses a hydraulically operable surgical stapler including a longitudinally flexible shaft for connecting the stapling section to the actuator section. The flexible shaft includes a first, flexible, small-diameter tube for transmitting hydraulic pressure contained in a stiffer, but flexible, second tube which gives the shaft the relatively slight degree of rigidity necessary to enable the flexible shaft to maintain a desired shape into which the shaft has been bent. The first and second tubes are contained in an outer sleeve which is secured to the stapling section and to the acutator section.

Hervas U.S. Pat. No. 4,962,877 discloses a hydraulic device including a flexible body for performing a surgical anastomosis. The body consists of three flexible hydraulic connecting tubes which are covered by a flexible plastic tube.

European Patent Application No. 293,123-A2 discloses a surgical anastomosis stapling apparatus including a stapling assembly comprising a tubular housing which supports an annular array of staples, a staple pusher mounted for movement between a retracted position within the housing and an extended position for expelling the annular array of staples, and a cylinder slidably mounted within the pusher assembly for selectively mounting either a trocar or an anvil assembly. The cylinder includes a central bore at its distal end for receiving a solid anvil shaft which is releasably held in the central bore by a detent formed on a spring member mounted at the distal end of the cylinder. The anvil shaft includes external longitudinal splines which engage internal splines provided within the housing for aligning the anvil shaft with the housing.

Co-pending U.S. application Ser. No. 590,404, filed Sep. 28, 1990, by Main and assigned to Ethicon, Inc., now U.S. Pat. No. 5,104,025, discloses a surgical stapling device including an anvil portion which is detachable from a stapling head portion containing a trocar tip upon which the anvil is attached. The anvil portion contains an elongated sleeve with an opening through which the trocar tip is inserted. The anvil is provided with a locking clip which releasably engages an indentation or ridge provided on the trocar tip which allows the anvil to be separated from the trocar tip.

SUMMARY OF THE INVENTION

The present invention achieves an improved surgical stapling instrument for applying surgical fasteners, such as staples, to human tissue which is particularly suited for performing a circular anastomosis stapling operation. The stapling instrument comprises a shaft assembly including a flexible support shaft for mounting a stapling head assembly on an actuator handle assembly. The stapling head assembly includes a staple holder for receiving one or more surgical staples, an anvil for clamping the tissue against the staple holder, and a staple driver for engaging and driving the staples from the staple holder into the tissue and against the anvil. The actuator handle assembly includes means for actuating the staple driver. The support shaft is flexible in any radial direction relative to its centerline into a curved configuration. The flexible support shaft is designed to be self-supporting and adapted to retain any curved configuration into which the support shaft is bent and to resist deflection when the stapling instrument is operated.

In a preferred embodiment of the stapling instrument, the flexible support shaft comprises one or more helical elements including a series of helical coils which are adapted to slidably engage each other with sufficient friction to resist deflection and to retain the curved configuration of the support shaft. A preferred embodiment of the flexible support shaft comprises first and second concentric helical elements each having a series of helical coils arranged with the coils of the first helical element interspersed with the coils of the second helical element. Each coil of the first helical element slidably engages the adjacent coils of the second helical element with sufficient friction to retain the support shaft in its curved configuration and to resist deflection.

The invention provides a surgical stapling instrument with a flexible support shaft which is malleable, i.e., the support shaft can be bent into any curvature appropriate for the anatomy of a specific surgical procedure. The flexible support shaft is flexible in all directions, i.e., both above and below the median plane of the stapling instrument and laterally to the left and right of the axis or centerline of the instrument. The flexible support shaft is capable of bending into compound curvatures and retaining itself in such curvatures. The flexible support shaft is designed to be self-supporting, i.e., the shaft can support itself in a straight or curved configuration without the requirement of a separate reinforcement or stiffening mechanism. When bent into a curved configuration, the flexible support shaft does not straighten when force is applied to the stapling head assembly during the clamping of the tissue and the firing of the staples.

In accordance with another aspect of the invention, the stapling head assembly is pivotally attached to the flexible support shaft so that the stapling head assembly is capable of pivoting relative to the axis or centerline of the support shaft. A remote actuator is provided on the actuator handle assembly to control the pivoting of the stapling head assembly relative to the support shaft. The flexibility of the support shaft and the pivotal movement of the stapling head assembly permit the surgical stapling instrument to assume any curved configuration suitable for performing an anastomosis on a patient.

In a preferred embodiment of the stapling instrument, the actuator handle assembly includes first actuator means for adjusting the gap between the anvil and the staple holder and second actuator means for actuating the staple driver. A tension member is contained within the flexible support shaft for transmitting tension from the first actuator means to the anvil to resist the forces exerted on the anvil when the staples are formed. A compression member is contained within the flexible support shaft for transmitting a compressive force from the second actuator means to advance the staple driver to drive the staples from the staple holder into the tissue and to form the staples against the anvil. The compression member comprises an outer flexible tubular cable extending longitudinally through the support shaft and the tension member comprises an inner flexible cable extending longitudinally through the outer tubular cable. The support shaft is flexible in any radial direction relative to its centerline into a curved configuration suitable for insertion into a patient. The flexible support shaft is adapted to support itself in any curved configuration and to resist deflection upon insertion into the patient and actuation of the stapling head assembly.

In accordance with another aspect of the invention, the stapling instrument includes shaft coupling means between the support shaft and the actuator handle assembly which compensates for differences in deflection of the tension and compression members relative to the support shaft. Preferably, a coupling member is slidably mounted on the actuator handle assembly and coupled to the support shaft. The coupling member is slidable longitudinally relative to the actuator handle assembly in response to changes in length of the tension and compression members when the staple driver is actuated. The tendency of the flexible support shaft to stretch during actuation of the staple driver is compensated by a compression spring which allows the coupling member to slide along the actuator handle assembly to avoid a tension load on the flexible support shaft.

According to another aspect of the invention, the actuator handle assembly includes anvil control means which is operable in two stages for moving the anvil relative to the staple holder of the stapling head assembly. The anvil control means has a first stage of operation in which the anvil is movable rapidly for opening and closing the anvil and a second stage of operation in which the anvil is movable gradually for clamping and unclamping the tissue. The anvil control means includes a thumb wheel rotatably mounted on the actuator handle assembly which actuates a slide mechanism connected to the anvil and slidably mounted for longitudinal movement along the actuator handle assembly. The thumb wheel is coupled to the slide mechanism by a two-stage transmission including a gear wheel mounted for rotation by the thumb wheel, a pin and slot connection for coupling the gear wheel to the slide mechanism in the first stage of operation, and a rack and pinion mechanism for coupling the gear wheel to the slide mechanism in the second stage of operation.

Another aspect of the invention relates to a stapling head assembly for a surgical instrument which includes an improved anvil gap adjusting mechanism. The stapling head assembly includes a casing, a staple holder mounted on the casing and having a plurality of slots for receiving the staples, an anvil mounted adjacent to the staple holder and having a plurality of staple forming grooves, and a staple driver slidably mounted in the casing for engaging and driving the staples from the staple holder into the tissue and against the anvil. The anvil is mounted on an anvil shaft for longitudinal movement relative to the casing. An anvil adjusting member is rotatably mounted on the casing and threadably coupled to the anvil shaft for moving the anvil longitudinally relative to the staple holder to adjust the anvil gap.

Preferably, the anvil gap adjusting mechanism is operable remotely via a rotatable adjusting knob on the acutator handle assembly which is connected to the adjusting member by a flexible tension-torsion cable contained within the flexible support shaft of the stapling instrument. The tension-torsion cable transmits both tension and torsion from the actuator handle assembly to the stapling head assembly to resist the forces exerted on the anvil by the staple driver when the staples are formed and to rotate the anvil adjusting member to adjust the anvil gap and select the height of the formed staples. Preferably, the tension-torsion cable is capable of transmitting torsion in both the clockwise and counterclockwise directions. The tension-torsion cable is contained within a tubular firing cable capable of transmitting compression from the actuator handle assembly to the stapling head assembly to actuate the staple driver. The actuator handle assembly includes a staple actuating lever for applying compression to the tubular firing cable which is transmitted to the staple driver to drive the staples from the staple holder and form the staples against the anvil.

In a preferred embodiment of the stapling head assembly, a trocar is threadably attached to the anvil adjusting member and connected to the anvil shaft. The trocar is slidably keyed to the casing and movable longitudinally relative to the casing when the adjusting member is rotated. The anvil shaft is adapted to be detachably connected to the trocar to permit the anvil to be detached from the stapling head assembly. A longitudinally extending guide tube is provided on the casing for receiving the anvil shaft. The anvil shaft and guide tube are provided with keyway means for rotationally aligning the anvil with the staple holder.

According to another aspect of the invention, the keyway means includes a plurality of internal circumferentially disposed longitudinal keys formed on the inside of the guide tube. A plurality of external circumferentially disposed longitudinal keys is formed on the anvil shaft which are received between the internal splines on the guide tube to align the staple forming grooves on the anvil with the staple receiving slots in the staple holder. One or more of the internal keys on the guide tube is longer than the remaining internal keys to provide at least one leader key for contacting one of the external keys to guide the anvil shaft into the guide tube. In one embodiment, the keyway means includes first and second leader keys which are longer than the remaining internal keys on the guide tube. The first leader key is longer than the second leader key and the second leader key is longer than the remaining internal keys on the guide tube. Preferably, the internal keys terminate in chisel points which are spaced proximally away from the distal end of the guide tube to avoid pinching of the tissue as the anvil shaft is retracted into the guide tube. The leader keys facilitate the entry of the anvil shaft into the guide tube and the alignment of the anvil with the staple holder.

The preferred embodiment of the stapling head assembly includes a plurality of locating fingers extending from the casing and adapted to engage and support the anvil adjusting member for rotation relative to the casing. The locating fingers are flexible outwardly to disengage the anvil adjusting member and allow the anvil to be displaced relative to the staple holder to open and close the stapling head assembly. The locating fingers provide a latch mechanism for latching the anvil adjusting member, the trocar and the anvil to the casing so that all tension forces are transmitted to the stapling head assembly through the tension-torsion cable. The anvil adjusting member is engaged by detents on the locating fingers when the the adjusting member and the anvil are moved into the closed position. The locating fingers are held in place by the driver assembly which slides forward to form the staples. The locating fingers provide a safety interlock feature to prevent the firing of the stapling head assembly until the adjusting member is latched by the locating fingers. The locating fingers when flexed outwardly engage and lock the driver assembly against longitudinal movement with the anvil in the open position. The driver assembly cannot be advanced until the anvil adjusting member is latched by the locating fingers with the anvil in the closed position.

In accordance with another aspect of the invention, the stapling head assembly is pivotally mounted on the support shaft assembly and a remote actuator is provided on the actuator handle assembly to control the pivoting of the stapling head assembly relative to the support shaft assembly. To control the movement of the anvil, separate actuators are provided on the actuator handle assembly for opening and closing the stapling head assembly and for adjusting the anvil gap. Also, an actuator in the form of a staple actuating lever is provided for actuating the driver assembly to drive the staples into the tissue and against the anvil.

Preferably, the stapling instrument includes an articulated pivot connection for coupling the tubular firing cable to the driver assembly of the stapling head assembly. The articulated pivot connection includes a hollow ball joint coupling member which is pivotally coupled at its opposite ends to the tubular firing cable and to the driver assembly. The tension-torsion cable extends through the ball joint coupling member. When the stapling head assembly is pivoted, the ball joint coupling member permits the tension-torsion cable to bend gradually through the articulated pivot connection to minimize friction and to avoid kinking of the cable.

According to another aspect of the invention, the stapling head assembly includes a tissue cutting and staple forming mechanism which is adapted to separate the cutting and forming forces to reduce the peak force required to cut and staple the tissue. The stapling head assembly includes a driver assembly comprising a knife driver for advancing a knife to cut the tissue and a staple driver for advancing the staples from the staple holder into the tissue and against the anvil. Driver coupling means is provided for coupling the knife driver and the staple driver together. The driver coupling means is adapted to disengage the staple driver from the knife driver when the tissue is cut by the knife to reduce the force required to actuate the driver assembly. Preferably, the driver assembly has a first stage of operation in which the staple driver and the knife driver are engaged and advanced together to drive the staples into the tissue, a second stage of operation in which the staple driver is disengaged from the knife driver when the tissue is cut, and a third stage of operation in which the staple driver is reengaged with the knife driver to form the staples against the anvil. As a result of the separation of the cutting and forming forces, the peak force required to operate the stapling head assembly is limited to the maximum of either the tissue cutting or the staple forming peak force.

In accordance with another aspect of the invention, the actuator handle assembly is ergonomically designed to facilitate the application and transmission of the required operating forces to the stapling head assembly of the stapling instrument. The actuator handle assembly is provided with actuator means having a first stage of operation in which the staple driver is advanced rapidly to drive the staples from the staple holder into the tissue and a second stage of operation in which the staple driver is moved gradually to form the staples against the anvil. In the preferred embodiment, the staple actuator means includes a staple actuating lever pivotally mounted on the actuator handle assembly and a cam follower assembly actuated by the staple actuating lever and coupled to the staple driver. The cam follower assembly is adapted to actuate the staple driver with a low mechanical advantage in the first stage of operation and a high mechanical advantage in the second stage of operation. When the actuator handle assembly is grasped in the open hand of a surgeon, only a small manual operating force is needed to pivot the staple actuating lever toward the actuator handle assembly to advance the staples into the tissue. As the staple actuating lever is pivoted toward the actuator handle assembly, the hand of the surgeon closes to a position in which a higher manual operating force can be applied to the staple actuating lever to cut the tissue and form the staples against the anvil.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view of a surgical stapling instrument constructed in accordance with this invention which includes a flexible support shaft for mounting a stapling head assembly on an actuator handle assembly;

FIG. 2 is a perspective view of the surgical stapling instrument with the flexible support shaft bent in a compound curvature and the stapling head assembly pivoted relative to the support shaft;

FIG. 3 is an enlarged, partially cutaway perspective view showing the flexible support shaft assembly of the surgical stapling instrument;

FIG. 4 is an enlarged cross section of the helical elements which form the flexible support shaft assembly;

FIG. 5 is an enlarged longitudinal section showing a portion of the flexible shaft assembly bent into a curved configuration;

FIG. 6 is a longitudinal, vertical section view of the stapling head assembly and flexible support shaft of the instrument of FIG. 1;

FIG. 7 is a longitudinal, vertical section view illustrating the fully open position of the stapling head assembly;

FIG. 8 is a longitudinal, vertical section view illustrating the stapling head assembly in its pivoted position;

FIG. 9 is an exploded perspective view illustrating the components of the stapling head assembly of FIG. 6;

FIG. 10 is an exploded perspective view of an anvil adjusting mechanism contained in the stapling head assembly of FIG. 6;

FIG. 11 is an enlarged partially cutaway top view of the anvil of the stapling head assembly;

FIG. 12 is an enlarged fragmentary section view of a cable coupling member of the stapling head assembly;

FIG. 19 is a partially cutaway side view of the actuator handle assembly of FIG. 1;

FIG. 20 is an end view of an anvil adjusting knob on the actuator handle assembly of FIG. 19;

FIG. 21 is a longitudinal, vertical section view of the actuator handle assembly of FIG. 19;

FIG. 22 is a front view of a cam follower assembly taken along line 22—22 of FIG. 21;

FIG. 28 is an enlarged side view of the anvil shaft of the stapling head assembly;

FIG. 29 is a proximal end view of the anvil shaft of FIG. 28;

FIG. 30 is a distal end view of the anvil shaft of FIG. 28;

FIG. 31 is an enlarged side view of the trocar of the stapling head assembly;

FIG. 32 is a proximal end view of the trocar of FIG. 31;

FIG. 33 is an enlarged distal end view of the staple holder of the stapling head assembly;

FIG. 34 is an enlarged proximal end view of the anvil of the stapling head assembly;

FIG. 35 is an enlarged, unwrapped view showing the internal splines on the guide tube of the stapling head assembly;

FIGS. 24-37 illustrate the staple forming action of the stapling head assembly;

FIG. 38 is a longitudinal section view illustrating another embodiment of the stapling head assembly;

FIG. 39 is a vertical section of the stapling head assembly taken along line 39—39 of FIG. 38;

FIG. 40 is a proximal end view of the trocar of FIG. 38;

FIG. 41 is a distal end view of the staple holder of FIG. 38; and

FIG. 42 is a proximal end view of the anvil of FIG. 38.

DETAILED DESCRIPTION OF PREFERRED EMBODIMENTS

Figure 13:
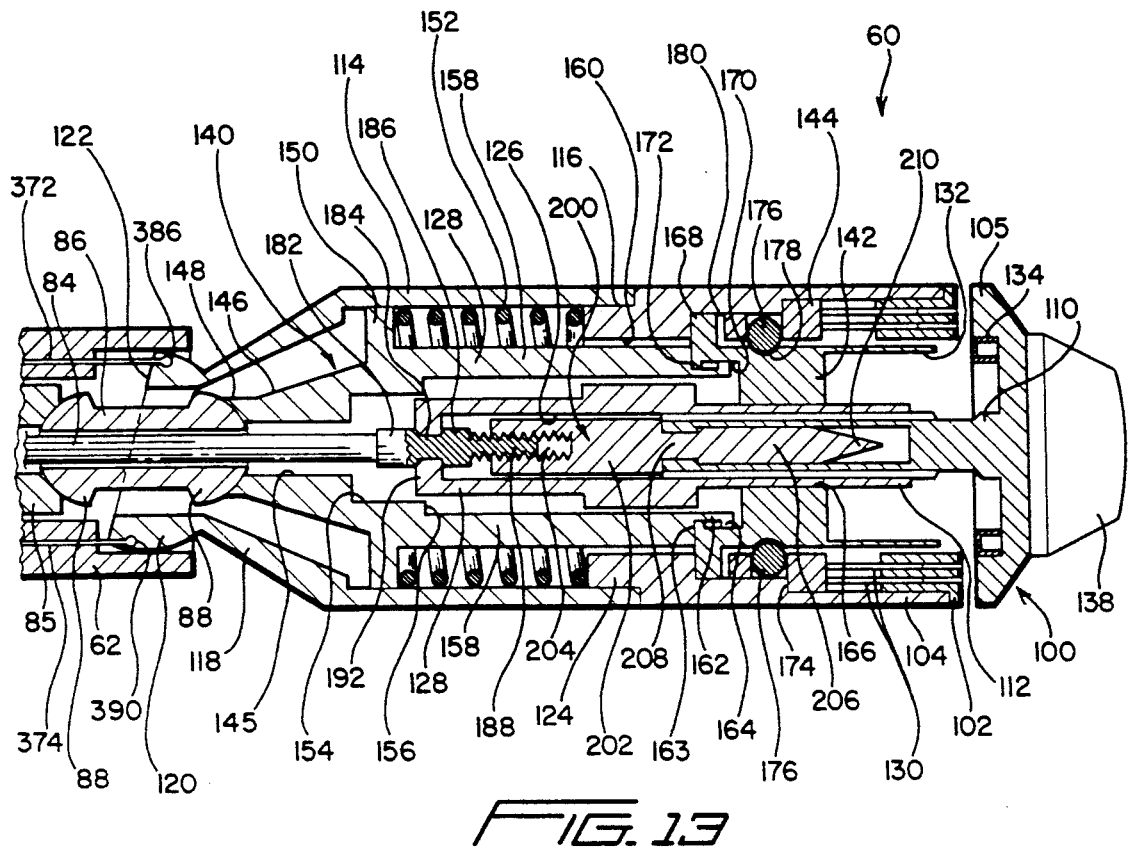
FIG. 13 is an enlarged longitudinal section view illustrating the ready to fire condition of the stapling head assembly.

Referring to FIG. 1, the present invention is embodied in a circular anastomosis surgical stapling instrument, generally 50, which includes a distal stapling head assembly 60 connected by a flexible shaft assembly 70 to a proximal actuator handle assembly 80. The flexible shaft assembly 70 is flexible in all directions, i.e., both above and below the median plane of the instrument and laterally to the right and left of the axis or centerline of the instrument. Also, as shown in FIG. 2, the stapling head assembly 60 is pivotally attached to the flexible shaft assembly 70 so that the stapling head assembly 60 is capable of pivoting vertically upward relative to the axis or centerline of the shaft assembly 70. The shaft assembly 70 is secured to a sleeve-like head joint 62 on which the stapling head assembly 60 is pivotally mounted by a pair of pivot pins 64. The flexibility of shaft assembly 70 and the pivotal movement of stapling head assembly 60 permit the surgical stapling instrument 50 to bend into any curved configuration suitable for performing an anastomosis on a patient.

The stapling instrument 50 includes an anvil assembly 100 which is slidable longitudinally relative to the stapling head assembly 60. The actuator handle assembly 80 includes an elongated handle 90 on which a staple actuating lever 92 is pivotally mounted. A rotatable thumb wheel 94 is provided at the top of the handle 90 for advancing and retracting the anvil assembly 100 relative to the stapling head assembly 60. An adjusting knob 96 is rotatably mounted at the rear of the handle 90 for adjusting the desired staple height by varying the gap between the anvil assembly 100 and the stapling head assembly 60. A pivotable control finger 98 is located at the top of the handle 90 behind the thumb wheel 94 for pivoting the stapling head assembly 60 relative to the shaft assembly 70.

As shown in FIG. 3, the flexible shaft assembly 70 comprises a first elongated helical element 71 and a second elongated helical element 72, including a plurality of helical coils 73 and 74, respectively, which are concentrically wound together with the coils 73 of helical element 71 alternately interspersed with the coils 74 of the helical element 72. As shown in FIG. 4, each coil 73 of the helical element 71 has a round cross section. Each coil 74 of the helical element 72 has a triangular cross section defining a set of inwardly sloped surfaces 76 and a flat outer surface 78. The sloped surfaces 76 of each coil 74 slidably engage the round surfaces 77 of the adjacent coils 73. The helical coil elements 71 and 72 allow the flexible shaft assembly 70 to be bent in any radial direction relative to its longitudinal axis or centerline into various curved configurations including the compound curves shown in FIG. 2. The flexible shaft assembly 70 is self-supporting and adapted to retain its curved configuration and to resist deflection. Each round coil 73 of the helical element 71 engages the adjacent triangular coils 74 of the helical element 72 with sufficient friction to retain the support shaft 70 in its curved configuration upon insertion into a patient and to resist deflection when the stapling head assembly 60 is actuated. The flexible shaft assembly 70 is covered by a flexible tubular sheath 75 having a smooth outer surface to facilitate the insertion of the stapling instrument 50 into the patient without tissue damage.

Referring to FIG. 5, the dual helical coil structure allows the flexible shaft assembly 70 to bend into a curved configuration by allowing the adjacent coils 73 and 74 to slide radially and to be displaced longitudinally relative to each other. Thus, when the flexible shaft assembly 70 is bent into a curved configuration, the portions of the coils 73 and 74 located on the outside of the curve are moved relative to each other such that the triangular coils 73 slide radially inward relative to the round coils 74. Also, on the outside of the curve, the round coils 73 and the triangular coils 74 are expanded longitudinally and the spacing between the adjacent coils is increased. On the other hand, the portions of the coils 73 and 74 at the inside of the curve are moved relative to each other such that the triangular coils 74 slide radially outward relative to the round coils 73. Also, on the inside of the curve, the round coils 73 and the triangular coils 74 are compressed longitudinally together and the spacing between the adjacent coils is decreased.

Referring to FIG. 6, inside the flexible tubular shaft assembly 70 is a tubular firing cable 82 for actuating the stapling head assembly 60. The firing cable 82 consists of a pair of helical metal bands 81 and 83 which are concentrically wound together with the coils of the helical band 81 alternately interspersed with the coils of the helical band 83. The metal bands 81 and 83 are tightly wound together into a dual helical coil structure which provides a flexible tubular member for transmitting compression to the stapling head assembly 60. An elongated cable 84 is mounted within the tubular firing cable 82 for transmitting tension and torsion to the stapling head assembly 60. Preferably, the inner cable 84 is a multi-stranded steel wire cable consisting of multiple layers of wire which are helically wound in opposite directions over an elongated flexible core 87 to provide a flexible tension-torsion member. The multiple wire windings in opposite directions enable the inner cable 84 to transmit torsion in both clockwise and counterclockwise directions relative to its axis.

The tubular firing cable 82 has its distal end received in a ferrule 85 which, in turn, engages a ball joint coupling member 86 for transmitting compression from the firing cable 82 to the stapling head assembly 60. The inner cable 84 extends through the ferrule 85 and the coupling member 86 for transmitting tension and torsion to the stapling head assembly 60. The coupling member 86 has a pair of semi-spherical flanges 88 at its opposite ends for pivotally connecting the ferrule 85 to the statpling head assembly 60. The coupling member 86 transmits the compression forces from the firing cable 82 to the stapling head assembly 60 and facilitates the bending of the tension-torsion cable 84 when the stapling head assembly 60 pivots relative to the shaft assembly 70 (FIG. 8).

As shown in FIG. 13, the stapling head assembly 60 includes a staple holder 102 mounted at the front end of a generally cylindrical and hollow casing 104. The staple holder 102 has a plurality of staple receiving slots 106 (FIG. 33) arranged in a circular array for receiving a plurality of surgical staples 65. Preferably, the staple receiving slots 106 are arranged in two closely spaced concentric annular rows. The anvil assembly 100 includes an anvil 105 located adjacent to the staple holder 102 and provided with a plurality of grooves 108 (FIG. 34) for forming the surgical staples 65. Preferably, the staple forming grooves 108 are arranged in two closely spaced concentric annular rows with each pair of grooves 108 aligned with a corresponding slot 106 in the staple holder 102. The anvil assembly 100 includes a central shaft 110 which is slidably received in an axially extending guide tube 112 provided on the casing 104. A set of external circumferentially disposed splines or keys 111 on the anvil shaft 110 engages a set of internal circumferentially disposed splines or keys 113 on the inside of the guide tube 112 for aligning the anvil 105 with the staple holder 102.

The casing 104 is supported by a hollow cylindrical housing 114 which is pivotally attached to the head joint 62 by the pivot pins 64. The casing 104 has a rear offset portion 116 which is reduced in diameter and received by the hollow cylindrical housing 114. At the rear of the housing 114 is a conically tapered portion 118 terminating in a flange 120 having an outer surface of hemi-spherical shape. The hemi-spherical flange 120 terminates at flat, annular rear edge 122 which is slanted at an angle of about 12½ degrees from a plane perpendicular to the longitudinal axis of the stapling head assemby 60. In the embodiment of FIG. 13, the front cylindrical casing 104 and the rear cylindrical housing 114 have an outer diameter of 33 millimeters.

The casing 104 includes a rear cylindrical wall 124 provided with a central circular bore 126. The guide tube 112 projects forwardly from the rear cylindrical wall 124 in axial alignment with the circular bore 126. The splines or keys 113 (FIG. 33) extend longitudinally along the inside of the guide tube 112 and into the circular bore 126. The anvil shaft 110 is received in the guide tube 112 which supports the anvil 100 in alignment with the staple holder 102. Also, a plurality of locating fingers 128 extend rearwardly from the cylindrical wall 124 in alignment with the circular bore 126. Preferably, a set of four locating fingers 128 is separated by four longitudinal slits 129 (FIG. 9) which allow the fingers 128 to flex radially outward relative to each other. The locating fingers 128 provide a latch mechanism which detachably connects the casing 104 to the tension-torsion cable 84. The fingers 128 also provide a safety interlock feature which is explained below.

Referring to FIG. 9, the stapling head assembly 60 includes a plurality of staple pusher bars 130 slidably mounted for longitudinal movement in the staple receiving slots 106 of the staple holder 102. The U-shaped surgical staples 65 are inserted into the slots 106 in front of the pusher bars 130. The staples 65 are arranged in two closely spaced concentric annular rows with the sharply pointed legs of each staple 65 pointing in the distal direction. The stapling head assembly 60 also contains an annular tissue cutting knife 132 which is concentric with and located inside the annular array of staples 65 in the staple holder 102. A sharpened front edge of the tissue cutting knife 132 points in the distal direction toward the anvil assembly 100 which supports an annular backup washer 134 (FIG. 11) aligned with the knife 132. The washer 134 has a channel-shaped cross section and provides an annular tissue cutting surface 136 against which the tissue is cut by the knife 132. A shroud 138 is attached to the anvil 105.

The stapling head assembly 60 includes a driver assembly comprising a main driver 140, a knife driver 142 and a staple driver 144 which are slidably mounted for longitudinal movement within the casing 104. The main driver 140 includes an axial bore 145 which extends through a conically shaped rear portion 146 of the main driver 140. A cylindrical flange 148 is provided at the rear of the conically shaped portion 146 of the main driver 140 for pivotally engaging the front hemi-spherical flange 88 of the ball joint coupling member 86. An annular flange 150 projects radially outward from the main driver 140. A compression spring 152 is interposed between the annular flange 150 and the cylindrical wall 124 of the casing 104. The spring 152 biases the main driver 140 rearwardly relative to the housing 114. The axial bore 145 in the main driver 140 extends into an enlarged counterbore 154 which has a sufficiently large diameter to normally receive the proximal ends of the locating fingers 128 of the casing 104. An annular ledge 156 (FIG. 18) is provided at the front edge of the counterbore 154 for engaging the proximal ends of the locating fingers 128 to prevent firing of the main driver 140 when the locating fingers 128 are flexed apart.

Referring to FIG. 9, the main driver 140 includes a plurality of elongated fingers 158 which slidably extend through a set of circular openings 160 provided in the rear cylindrical wall 124 of the casing 104. In the preferred embodiment, a set of four driver fingers 158 is provided on the main driver 140 which are received in four openings 160 spaced at equal angular intervals on the casing 104. A narrow extension 162 projects forwardly from the front edge of each driver finger 158. A lug 164 projects radially outward at the front of each extension 162.

The knife driver 142 consists of a cylindrical body provided with an axial bore 166 which slidably receives the guide tube 112 and allows the knife driver 142 to slide along the guide tube 112 relative to the casing 104. The annular knife 132 is secured to the front of the knife driver 142 by a pair of screws 135. An annular flange 168 which surrounds a counterbore 170 is formed at the rear of the knife driver 142. The counterbore 170 is sufficiently large in diameter to receive the finger extensions 162 but not to receive the driver fingers 158. The front edges 163 (FIG. 13) of the driver fingers 158 engage the rear surface of the flange 168 when the main driver 140 and the knife driver 142 are in the ready to fire position. An annular lip 172 projecting radially inward from the flange 168 is engaged by the lugs 164 on the finger extensions 162 to move the knife driver 142 rearwardly when the main driver 140 is retracted.

Referring to FIG. 9, the staple driver 144 is annular in shape and provided with a series of circumferentially spaced sockets 174 for receiving a plurality of balls 176. Preferably, a set of eight balls 176 is received in a set of eight sockets 174 spaced at equal angular intervals on the staple driver 144. The knife driver 142 is generally cylindrical in shape and is slidably received within the annular staple driver 144. The knife driver 142 includes a circumferential groove 178 formed in its outer surface for receiving the balls 176. The balls 176 are initially held in the circumferential groove 178 by an inner cylindrical wall 180 (FIG. 13) of the casing 104 so that the knife driver 142 and the staple driver 144 are coupled together by the balls 176. The staple driver 144 engages the staple pusher bars 130 which extend into the staple receiving slots 106 to drive the staples 65 from the staple holder 102 when the staple driver 144 is advanced.

As shown in FIG. 13, the stapling head assembly 60 includes a cable coupling member 182 which is secured, e.g., by brazing or welding, to the distal end of the tension-torsion cable 84 and detachably connected to the casing 104 by the locating fingers 128. The cable coupling member 182 is generally cylindrical in configuration and provided with a circumferential groove 184 (FIG. 12) adjacent to an annular flange 186. A threaded shank 188 projects forwardly from the flange 186. The groove 184 has a rear conically tapered surface 190. The four locating fingers 128 (FIG. 9) are configured to provide a cylinder-like extension projecting rearwardly from the casing 104 and are adapted to capture the cable coupling member 182 by engaging the annular groove 184. An inwardly projecting detent 192 (FIG. 12) at the rear of each locating finger 128 is adapted to be received in the circumferential groove 184 formed in the cable coupling member 182. Each detent 192 includes an inner vertical edge 194 for engaging the annular flange 186. The detent 192 also has an outer sloped edge 196 for engaging the rear tapered surface 190 of the annular groove 184.

Referring to FIG. 13, a trocar 200 located within the axial bore 126 in the housing 104 serves to connect the anvil assembly 100 to the cable 84. The trocar 200 includes a rear cylindrical section 202 provided with a threaded axial bore 204 (FIG. 10) for receiving the threaded shaft 188 formed at the front of the cable coupling member 182. The trocar 200 includes a front cylindrical section 206 which is smaller in diameter than the rear cylindrical section 202. A shank section 208 of reduced diameter connects the front cylindrical section 206 to the rear cylindrical section 202. A tapered annular shoulder 209 (FIG. 31) is formed at the rear of the front cylindrical section 206 adjacent to the shank section 208. The front cylindrical section 206 is conically tapered to define a pointed trocar tip 210.

As shown in FIG. 10, the anvil shaft 110 has a plurality of longitudinal slits 101 extending from its proximal end which divide the anvil shaft 110 into a set of elongated, resilient fingers 103. Preferably, the anvil shaft 110 is divided by the longitudinal slits 101 into four fingers 103 which can be flexed apart by the trocar tip 210 to allow the trocar 200 to be inserted in and removed from the anvil shaft 110. Each elongated finger 103 has an inwardly facing ledge 107 (FIG. 28) at its proximal end for engagement with the shank section 208 (FIG. 31) of the trocar 200. Each ledge 107 has a sloped rear edge 109 for engaging the tapered annular shoulder 209 on the front cylindrical section 206 of the trocar 200. When the trocar 200 is inserted into the anvil shaft 110, the proximal ledges 107 of the fingers 103 snap together around the shank 208 section to rotatably connect the anvil shaft 110 to the trocar 200.

The trocar 200 is slidably keyed to the casing 104 by a plurality of longitudinal splines or keys 212 (FIG. 31) formed on the outer surface of the rear cylindrical section 202. The trocar splines 212 are received between the splines or keys 113 formed on the inside of the guide tube 112 when the trocar 200 is retracted into the central bore 126 of the casing 104. Because the rear cylindrical section 202 is slidably keyed to the casing 104, the trocar 200 can be moved longitudinally in the guide tube 112 but the trocar 200 cannot rotate about its axis. Also, the anvil shaft 110 is slidably keyed to the casing 104 by a plurality of longitudinal splines or keys 111 (FIG. 28) formed on the outer surface of the shaft 110. The anvil splines 111 are received between the splines or keys 113 formed on the inside of the guide tube 112 when the anvil shaft 110 is retracted into the central bore 126 of the casing 104. Because the anvil shaft 110 is keyed to the casing 104, the staple forming grooves 108 on the anvil 105 are aligned with the staple receiving slots 106 provided in the staple holder 102.

Referring to FIG. 13, with the anvil assembly 100 in the closed position, the locating fingers 128 engage and support the cable coupling member 182 for rotation relative to the casing 104. The cable coupling member 182 when rotated acts as a cable adjusting member in the stapling head assembly 60 to adjust the anvil gap. When the cable coupling member 182 is rotated by the tension-torsion cable 84, the rotation of the threaded shank 188 results in longitudinal movement of the trocar 200 along the guide tube 112. The longitudinal movement of the trocar 200 is transmitted via the anvil shaft 110 to adjust the gap between the anvil 105 and the staple holder 102 to select the staple height to be produced when the stapling head assembly 60 is fired.

Figure 14:
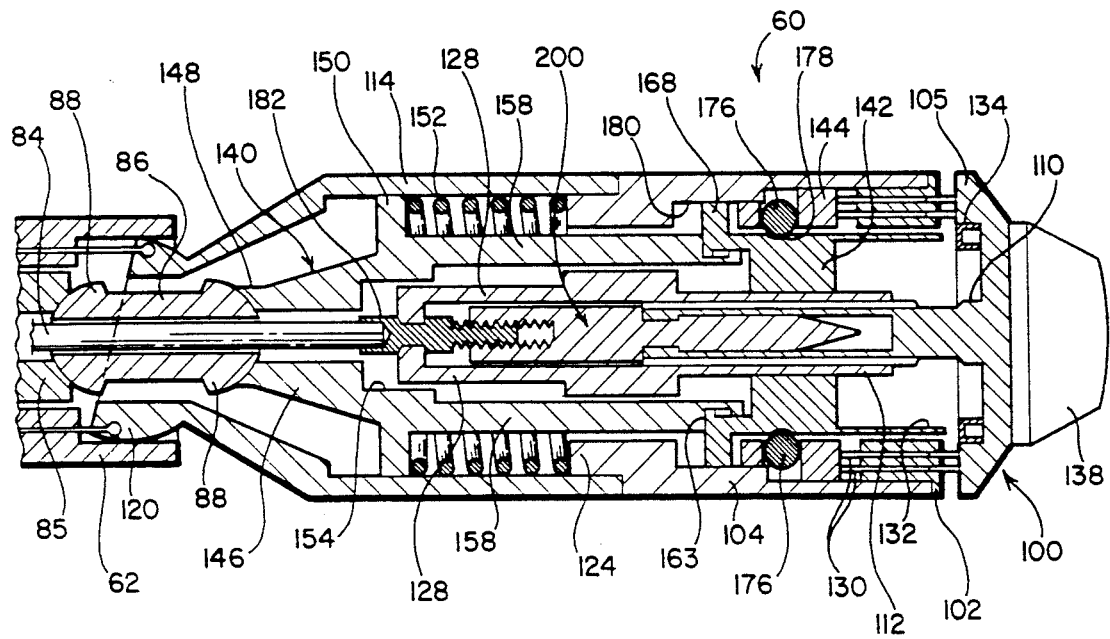
FIG. 14 is an enlarged longitudinal section view illustrating an initial stage of the operation of the stapling head assembly.
Figure 15:
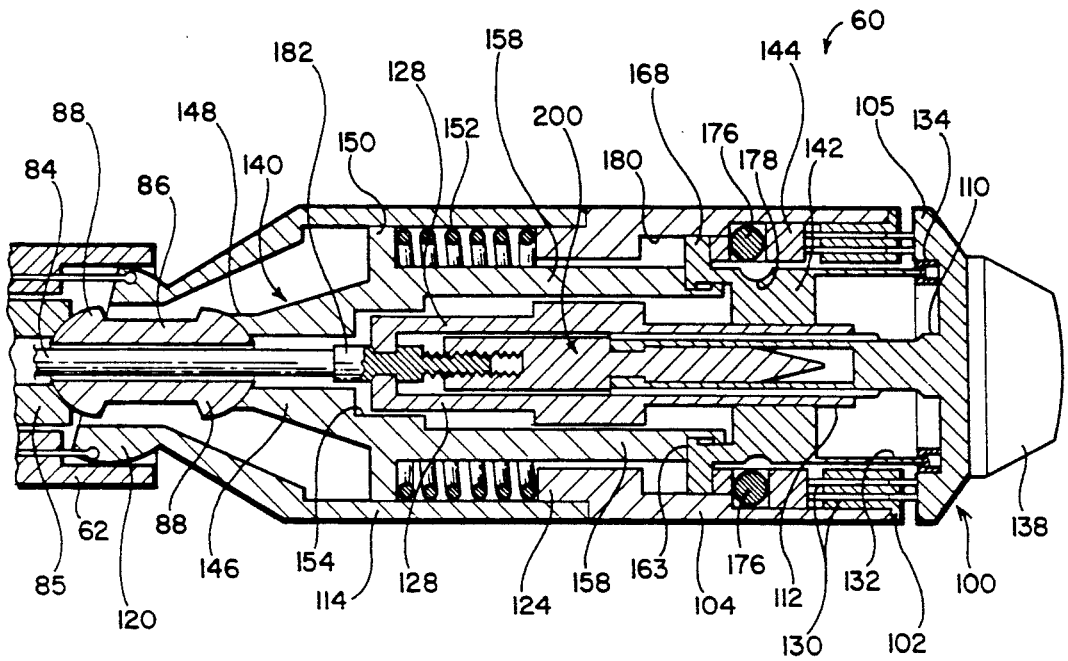
FIG. 15 is an enlarged longitudinal section view illustrating an intermediate stage of the operation of the stapling head assembly.

Referring to FIGS. 13-15, the locating fingers 128 provide a latch mechanism for latching the cable coupling member 182, the trocar 200 and the anvil shaft 110 to the casing 104 so that all tension forces are transmitted to the stapling head assembly 60 through the tension-torsion cable 84. With the anvil assembly 100 in a closed position, the detents 192 on the locating fingers 128 are engaged in the annular groove 184 on the cable coupling member 182. Also, the locating fingers 128 are received within the counterbore 154 in the main driver 140. As the main driver 140 is advanced, the locating fingers 128 are confined within the counterbore 154 so that the detents 192 remain in engagement with the annular groove 184 of the cable coupling member 182. As a result, the cable coupling member 182 is latched by the locating fingers 128 to the casing 104. Thus, all tension forces applied to the tension-torsion cable 84 are transmitted via the cable coupling member 182 to the stapling head assembly 60.

Figure 18:
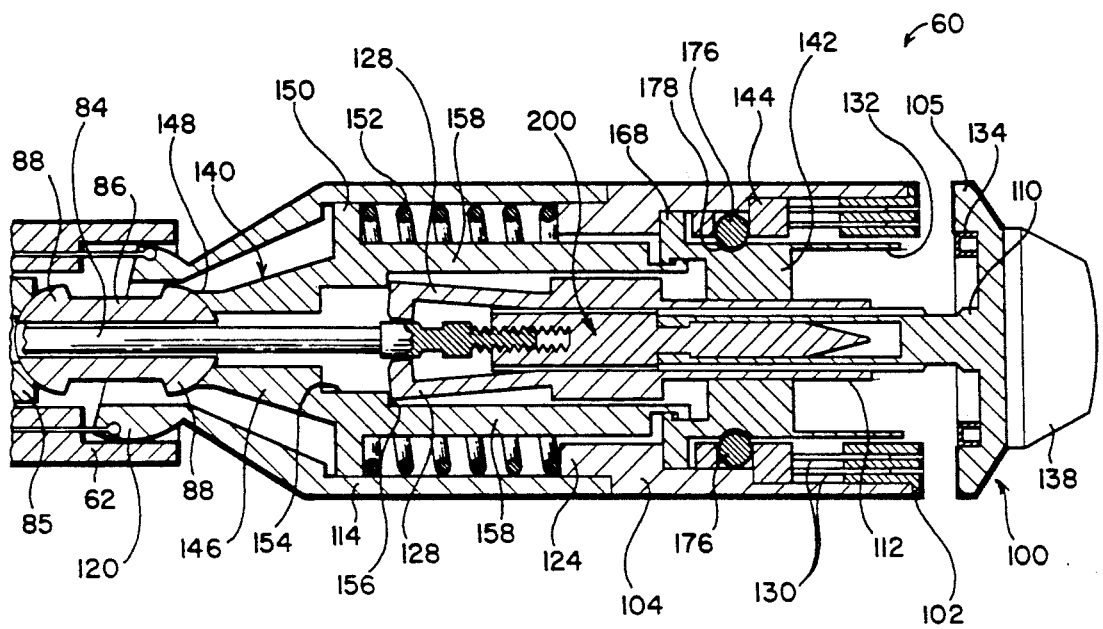
FIG. 18 is an enlarged longitudinal section view of the stapling head assembly illustrating the firing safety interlock feature of the instrument.

As shown in FIG. 18, the locating fingers 128 also provide a safety interlock feature which prevents the firing of the stapling head assembly 60 until the cable coupling member 182 is latched by the locating fingers 128. With the anvil assembly 100 in an open position, the locating fingers 128 are flexed radially apart by the cable coupling member 182, or by the tension-torsion cable 84. The locating fingers 128 when flexed apart engage the annular ledge 156 and lock the main driver 140 against longitudinal movement while the anvil assembly 100 is in an open position. The main driver 140 cannot be advanced until the cable coupling member 182 is latched by the locating fingers 128 with the anvil assembly 100 in the closed position.

As shown in FIG. 33, twenty-eight staple receiving slots 106 are provided in the staple holder 102 which are arranged in two concentric annular rows with fourteen slots 106 in each row. On the anvil 105 (FIG. 34), twenty-eight pairs of staple forming grooves 108 are also arranged in two concentric annular rows in alignment with the staple receiving slots 106 of the staple holder 102. A set of seven internal splines or keys 113 (FIG. 33) is provided on the guide tube 112 at equally spaced intervals. Also, a set of fourteen external splines or keys 111 (FIG. 34) is provided on the anvil shaft 110 at equally spaced intervals. When the anvil shaft 110 is retracted into the guide tube 112, the external splines 111 on the anvil shaft 110 are received between the internal splines 113 on the guide 112 to provide precise circumferential alignment of the anvil 100 with the staple holder 102. As a result, the staple forming grooves 108 on the anvil 102 are accurately aligned with the staple receiving slots 106 in the staple holder 102.

As shown in FIG. 35, the internal splines 113 terminate in chisel points 115 which are spaced proximally away the distal end of the guide tube 112. This placement of the internal splines 113 reduces the tendency of the purse stringed tissue to be pinched between the internal splines 113 and the external splines 111 and 212 as the anvil shaft 110 and the trocar 200 are retracted and prevent the tissue from being pulled into the guide tube 112. Also, as shown in FIG. 7, the distal end of the guide tube 112 is disposed adjacent to the staple holder 102 to push the tissue over the external splines 111 and 212 as the anvil shaft 110 and the trocar 200 are retracted to prevent the tissue from being pulled into the hollow interior of the casing 104. The guide tube 112 provides enhanced visibility as the anvil shaft 110 and the trocar 200 are retracted into the stapling head assembly 60.

Referring to FIG. 35, two of the internal splines or keys 113' and 113" are longer than the remaining splines or keys 113 on the guide tube 112. For example, the first key 113' has its chisel point 115' located about 0.030 inch above the chisel point 115" of the second key 113" which, in turn, is located about 0.030 inch above the level of the chisel points 115 on the other keys 113. If desired, the chisel points 115 on the lowermost keys 113 can be eliminated. The longer keys 113' and 113" eliminate the need for excessively tight tolerances on the location and shape of the chisel points 115.

If all seven keys 113 are provided with chisel points 115 at the same level, it possible that one or more of the keys 113 will attempt to align the anvil shaft 110 in one direction while the other keys 113 will attempt to turn the anvil shaft 110 in the other direction resulting in the possibility of locking, binding or breaking of the stapling instrument 50. This problem of multiple point contact may arise when all of the chisel points 115 engage the splines 111 on the anvil shaft 110 at the same time.

In the present arrangement, the longer keys 113' and 113" are used as leaders to avoid the problem of multiple point contact. By allowing only one of the chisel points 115' of the first leader key 113' to make the initial contact with the anvil splines 111, the possibility of having two or more chisel points 115 working in opposite directions is eliminated. The second leader key 113" provides for the instance when the first leader key 113' moves into one of the longitudinal slits 101 of the anvil shaft 110. Since there is no initial alignment from the first leader key 113' in this instance, the problem of multiple point contact can occur if only one leader key 113' is used. However, the provision of the second leader key 113" eliminates this possibility since no two keys 113 can be aligned with the longitudinal slits 101 in the anvil shaft 110 at the same time. It is noted that any one of the keys 113 can be used as the second leader. Thus, it is not necessary that the leader keys 113' and 113" be located adjacent to each other.

As shown in FIG. 28, the anvil shaft 110 includes a circumferential notch 117 adjacent to the anvil 105. The notch 117 provides a convenient area for the purse stringing of the tubular tissue to be anastomosed. If the tissue is tightly purse stringed to the shaft 110 in the circumferential notch 117, the purse stringed tissue cannot easily slip over the splines 111 on the anvil shaft 110. As a result, the purse stringed tissue is confined to the distal region of the anvil shaft 110 beyond the splines 111 and the anvil shaft 110 will not inadvertently slip through the purse stringed tissue.

As shown in FIG. 11, the anvil shaft 110 has an internally threaded bore 119 at its distal end for receiving a screw 121- which fastens the anvil 100 to the anvil shaft 110. A pair of flat lands 123 is provided on the opposite sides of the anvil shaft 110 which enable the anvil shaft 110 to be firmly gripped, e.g., by a placement mechanism (not shown), as the screw 121 is threaded into the bore 119. At the distal end of the shaft 110 is a key-shaped extension 125 (FIG. 30) with flat opposed sides 127 which is received in a key-shaped opening in the anvil 105 for circumferential alignment of the splines 111 on the anvil shaft 110 with the staple forming grooves 108 on the anvil 105.

In the preferred embodiment of the stapling head assembly 60, the casing 104 is made of plastic material which allows the locating fingers 128 to flex outwardly to receive the cable coupling member 182 therebetween. The staple holder 102 is also made of plastic material. The anvil 100 and the housing 114 are formed of metal, e.g., aluminum or stainless steel. Also, the tissue cutting knife 132 and the drivers 140, 142 and 144 are made of metal, e.g., aluminum or stainless steel.

Referring to FIGS. 19 and 21, the actuator handle assembly 80 is shown in the ready to fire condition. The staple actuating lever 92 is pivotally mounted on a shaft 230 which extends transversely between the opposite sides of the handle 90. Also, a pair of Geneva gear wheels 232 are rotatably mounted on the shaft 230 on opposite sides of the staple actuating lever 92. The staple actuating lever 92 is bifurcated at the top and supports a cam 234 for actuating a cam follower assembly 235 when the lever 92 is pivoted. The cam follower assembly 235 includes a cam follower 236 and a pusher block 238 which are slidably mounted for longitudinal movement relative to the handle 90. The cam follower assembly 235 causes a compressive force to be exerted on the tubular firing cable 82, which force is transmitted to the stapling head assembly 60.

Figures 23, 24:
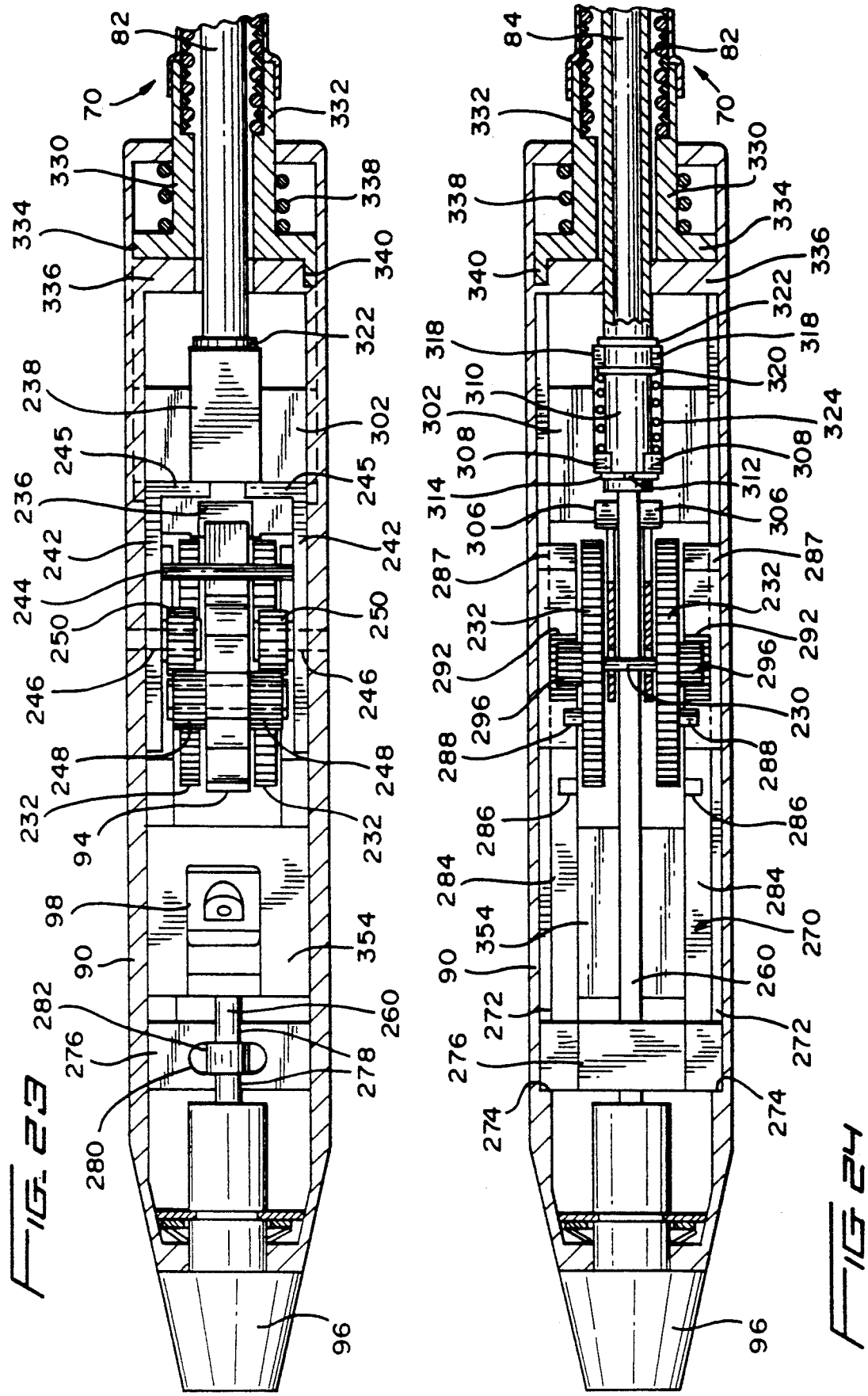
FIG. 23 is a partially cutaway top view of the actuator handle assembly of FIG. 19.
FIG. 24 is a partially cutaway bottom view of the actuator handle assembly of FIG. 19.

The thumb wheel 94 is rotatably mounted by a shaft 240 extending between a pair of pivot arms 242 which are joined together by a cross link 244. Each pivot arm 242 is provided with a latching finger 245 at its distal end which precludes operation of the cam follower 236 when the thumb wheel 94 is actuated. The pivot arms 242 are pivotally mounted on a pair of shafts 246 which extend inwardly from the opposite sides of the handle 90. The thumb wheel 94 supports a pair of drive gears 248 on its opposite sides which are mounted on the shaft 240 for rotation with the thumb wheel 94. The drive gears 248 mesh with a corresponding pair of pinion gears 250 rotatably mounted on the same shafts 246 which support the pivot arms 242 on opposite sides of the handle 90. As shown in FIG. 23, the pinion gears 250 are spaced apart to accomodate the thumb wheel 94 therebetween. The pinion gears 250 mesh with the outer circumferential teeth 233 (FIG. 19) on the Geneva wheels 232.

Figure 25:
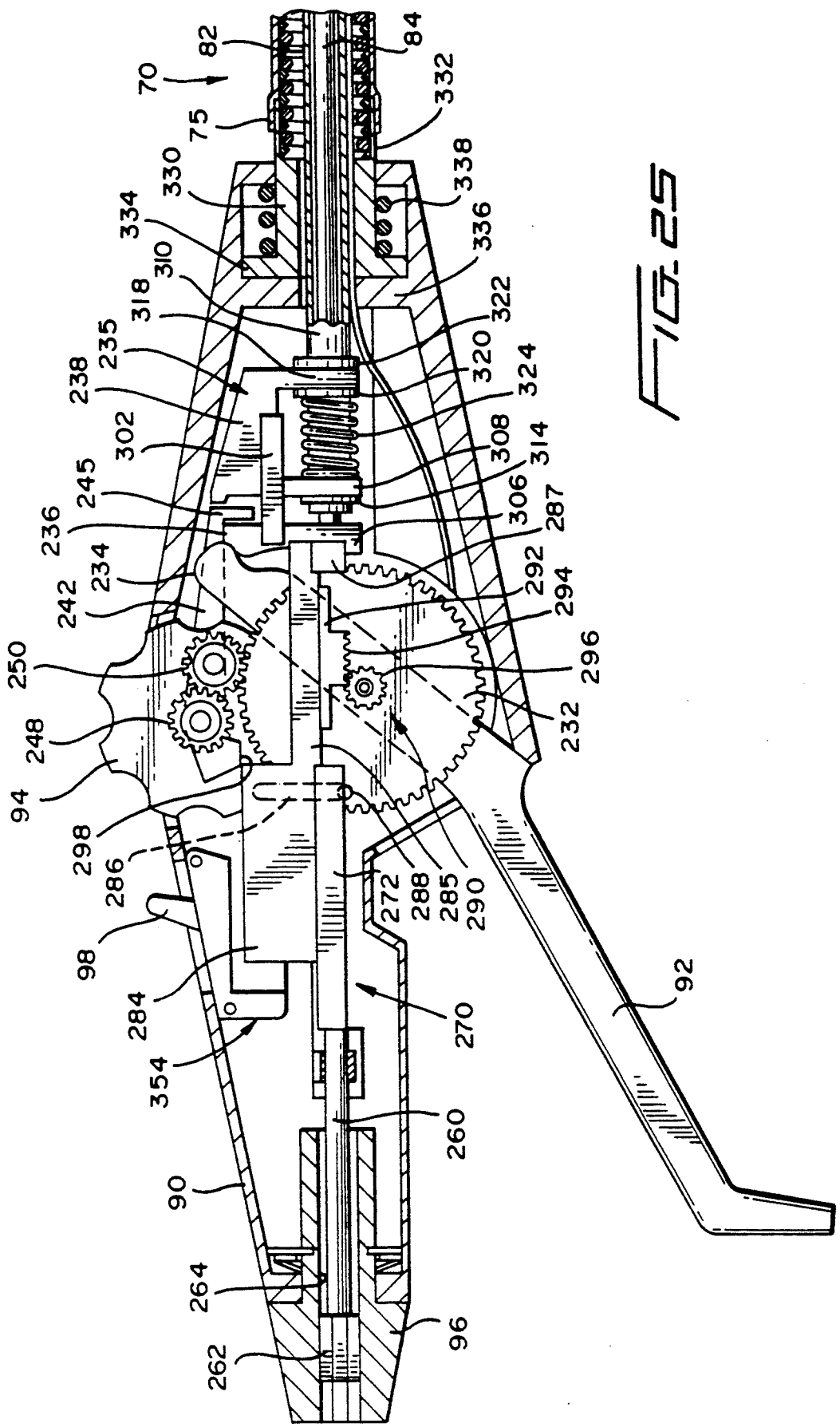
FIG. 25 is a longitudinal section view of the actuator handle assembly illustrating the anvil advancing mechanism partially advanced.

Both the thumb wheel 94 and the drive gears 248 are carried by the pivot arms 242. Normally, as shown in FIG. 19, the pivot arms 242 are oriented such that the thumb wheel 94 is pivoted downward with the pinion drive gears 248 engaged with the teeth 233 at the periphery of the Geneva gear wheels 232. Since the drive gears 248 and the pinion gears 250 mesh with each other and with the peripheral teeth 233 of the Geneva gear wheel 232, each Geneva gear wheel 232 is normally locked against rotation. However, the pivot arms 242 allow the thumb wheel 94 to pivot upwardly, as shown in FIG. 25, to move the drive gears 248 out of engagement with the peripheral teeth 233 of the Geneva wheels 232. When the thumb wheel 94 is rotated, the drive gears 248 impart rotation to the pinion gears 250 which, in turn, rotate the Geneva gear wheels 232. The latching fingers 245 are pivoted downward in front of the cam follower 236 to prevent actuation of the can follower assembly 235 by the staple actuating lever 92.

The actuator handle 90 supports an elongated control rod 260 (FIG. 21) having its front end secured, e.g., by brazing or welding, to the inner tension-torsion cable 84. The control rod 260 is secured at its rear end to a sleeve 262 which is slidably received in an axial passageway 264 formed in the adjusting knob 96. The sleeve 262 is keyed to the passageway 264 such that the control rod 260 is slidably coupled to the adjusting knob 96 for simultaneous rotation therewith. For example, as shown in FIG. 20, the sleeve 262 and passageway 264 are hexagonal in configuration to couple the control rod 260 for rotation with the adjusting knob 96.

As shown in FIG. 24, the control rod 260 is slidably supported for longitudinal movement along the handle 90 by a slide mechanism 270 including a pair of elongated slide members 272 which are slidably mounted in longitudinal grooves 274 formed in the opposite sides of the actuator handle 90. The slide members 272 are coupled together at the rear by a bracket 276. A pair of notches 278 (FIG. 23) is formed at the front and rear of the bracket 276 for receiving the control rod 260. The bracket 276 includes a transverse slot 280 which intersects the front and rear notches 278. The transverse slot 280 receives a boss 282 formed on the control rod 260 to connect the control rod 260 to the bracket 276 and to the slide members 272 for longitudinal movement therewith. Each slide member 272 is attached to an upstanding flange 284 (FIG. 19) having an extension bar 285 coupled to a slide block 287 slidably received in the corresponding longitudinal groove 274 in the handle 90. Each flange 284 (FIG. 19) is provided with a vertical slot 286 for receiving a drive pin 288 mounted on each Geneva wheel 232. During rotation of the Geneva wheels 232, the drive pins 288 enter the vertical slots 286 formed in the flanges 284 to move the slide members 272 longitudinally relative to the actuator handle 90. The pin and slot mechanisms provide a low mechanical advantage which enables the anvil 100 to be moved rapidly relative to the staple holder 102 in response to rotation of the thumb wheel 94.

In addition, a rack and pinion mechanism 290 is provided for coupling each slide member 272 to the corresponding Geneva gear wheel 232. Each rack and pinion mechanism 290 includes a rack 292 on the underside of the extension bar 285 provided with a row of teeth 294 for engaging a pinion gear 296 mounted on shaft 230 for rotation with Geneva gear wheel 232. The rack and pinion mechanisms 290 provide a high mechanical advantage which enables the anvil 105 to be moved gradually relative to the staple holder 102 in response to rotation of the thumb wheel 94.

In response to the clockwise rotation of the thumb wheel 94 (FIG. 25), the pivot arms 242 are pivoted clockwise about the shafts 246 to lift the drive gears 248 away from engagement with the peripheral teeth 233 of the Geneva gear wheels 232. As a result, the Geneva gear wheels 232 are unlocked for rotation by the thumb wheel 94. The cam follower assembly 235 is latched by the latching fingers 245. The clockwise rotation of the thumb wheel 94 is converted via the drive gears 248 and the pinion gears 250 into clockwise rotation of the Geneva gear wheels 232 to advance the slide mechansim 270. As the slide mechanism 270 is advanced, each flange 284 slides underneath a cam surface 298 at the proximal end of each pivot arm 242 to retain the drive gears 248 in the unlocked position and to retain the latching fingers 245 in front of the cam follower 236.

Initially, in the first stage of operation (FIG. 25), the slide mechanism 270 and the control rod 260 are advanced by the rack and pinion mechanisms 290. The clockwise rotation of each Geneva gear wheel 232 is transmitted by the pinion gear 296 and the rack 292 into longitudinal movement of each slide member 272 to gradually advance the control rod 260. The motion of the control rod 260 is transmitted via the tension-torsion cable 84 to the stapling head assembly 60 to gradually advance the anvil 105 away from the staple holder 102.

Subsequently, in the second stage of operation (FIG. 26), the drive pin 288 on each Geneva gear wheel 232 enters the vertical slot 286 formed in the flange 284. The counterclockwise rotation of the Geneva gear wheel 232 is transmitted by the pin 288 and the slot 286 into longitudinal movement of each slide member 272 to rapidly advance the control rod 260. The motion of the control rod 260 is transmitted via the tension-torsion cable 84 to the stapling head assembly to rapidly move the anvil 105 away from the staple holder 102.

As shown in FIG. 22, the cam follower 236 is mounted on a rectangular slide member 302 which is slidably received in a pair of longitudinal grooves 304 formed in opposite sides of the actuator handle 90. At the rear of the slide member 302 is a first pair of depending fingers 306 (FIG. 24) which slidably receive the tension-torsion cable 84 therebetween. A second pair of depending fingers 308 is centrally located on the slide member 302 and spaced distally from the depending fingers 306. An actuator sleeve 310 is slidably received between the depending fingers 308 and is secured at its distal end to the tubular firing cable 82. An annular groove 312 is formed at the proximal end of the actuator sleeve 310 and a C-shaped retainer clip 314 is snap fitted into the annular groove 312 to retain the proximal end of the actuator sleeve 310 in the space between the depending fingers 306 and 308.

As shown in FIGS. 21 and 22, the pusher block 238 for actuating the tubular firing cable 82 is slidably mounted on the slide member 302 of the cam follower 236. The pusher block 238 includes a pair of longitudinal channels 316 extending along its opposite sides which slidably mount the pusher block 238 on a pair of inwardly projecting ledges 316 provided on opposite sides of the slide member 302. Also, the pusher block 238 includes a pair of depending arms 318 which span the actuator sleeve 310. The depending arms 318 are received between a pair of spaced, annular flanges 320 and 322 on the actuator sleeve 310. A compression spring 324 is interposed between the depending fingers 308 and the proximal flange 320 on the actuator sleeve 310. The compression spring 324 normally exerts a biasing force on the actuator sleeve 310 and the pusher block 238 to urge the cam follower 236 and the pusher member 238 apart and to maintain the retainer clip 314 at the rear of the sleeve 310 engaged with the depending fingers 308.

Figure 27:
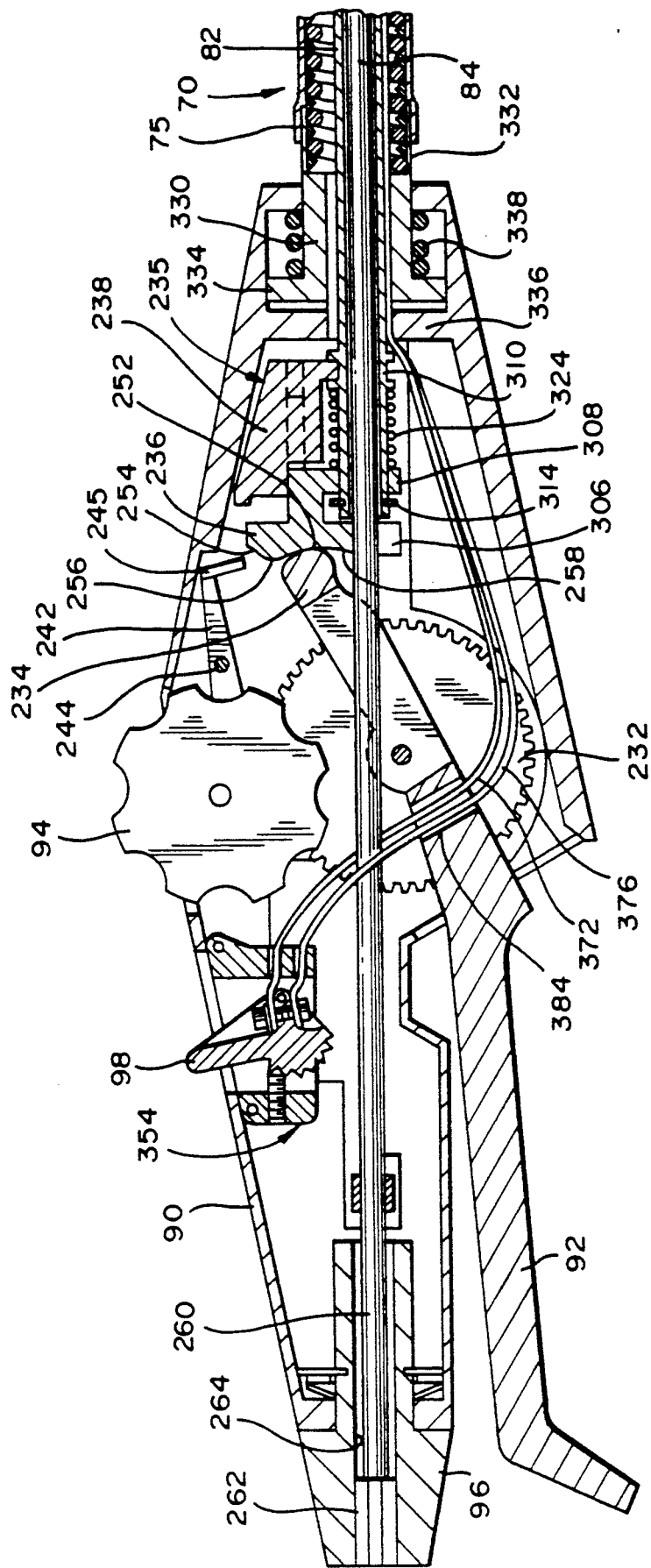
FIG. 27 is a longitudinal section view of the actuator handle assembly illustrating the operation of the staple actuating lever.

Referring to FIG. 27, the cam 234 includes a rounded nose 252 for engaging a rear, profiled edge of the cam follower 236 which includes an upper inclined cam surface 254, a convex cam surface 256, and a concave cam surface 258. When the staple actuating lever 92 is pivoted clockwise, as viewed in FIG. 27, the cam nose 252 travels downward along the inclined cam surface 254 to advance the cam follower 236 longitudinally relative to the handle 90. The motion of the cam follower 236 in the proximal direction is transmitted via the compression spring 324 to the pusher block 238 which, in turn, advances the actuator sleeve 310 longitudinally relative to the handle 90. The longitudinal movement of the actuator sleeve 310 is transmitted via the compression member 82 to the main driver 140 (FIG. 9) of the stapling head assembly 60. In the initial operating stage of the cam follower assembly 235, the inclined cam surface 254 provides a low mechanical advantage for rapidly advancing the main driver 140, the knife driver 142 and the staple driver 144 to drive the staples from the staple holder 102 into the tissue.

Referring to FIG. 27, when the cam nose 252 arrives at the convex cam surface 256 on the cam follower 236, the first operating stage of the cam follower assembly 235 is completed and the second operating stage is ready to begin. As the cam nose 252 travels downward over the concave cam surface 258, the cam follower assembly 235 is further advanced in the longitudinal direction with a high mechanical advantage for gradually advancing the main driver 140, which, in turn, actuates the knife driver 142 and the staple driver 144. The concave cam surface 258 is shaped to provide a high mechanical advantage for advancing the cam follower assembly 235 in response to pivotal movement of the staple actuating lever 92.

As shown in FIG. 13, with the main driver 140 in the ready-to-fire position, the front edges 163 of the driver fingers 158 engage the flange 168 at the rear of the knife driver 142. The lugs 164 on the driver finger extensions 162 are displaced forwardly from the annular lip 172 on the driver 142. At this point, the knife driver 142 and the staple driver 144 are coupled together by the balls 176 which are located in the sockets 174 and are held in the annular groove 178 by the annular ledge 179 formed inside the casing 104. When the main driver 140 is advanced, the knife driver 142 and the staple driver 144 are advanced together until the balls 176 are freed from the ledge 180 (FIG. 14). At this point, the staples 65 penetrate into the tissue and the knife 132 is ready to begin to cut the tissue adjacent to the staples.

Referring to FIG. 15, as the main driver 140 is further advanced, the balls 176 move radially outward in the sockets 174 away from the annular groove 178 to disengage the staple driver 144 from the knife driver 142. As the main driver 140 continues to advance, the knife driver 142 advances the annular knife 132 to cut through the tissue and into the backup washer 134. While the the tissue is cut, the staple driver 144 remains stationary to hold the staples 65 in the tissue and no staple formation occurs. As a result, the compressive force applied to the main driver 140 is transmitted to the knife driver 142 to advance the knife 132 and cut the tissue. At this point, no additional force is required to form the staples which are merely held in the tissue by the staple driver. Consequently, the peak force required to actuate the driver assembly is reduced because the staples are not formed at the same time that the tissue is being cut.

After the knife 132 cuts through the tissue and into the backup washer 134, the staple driver 144 is reengaged by the annular flange 168 on the knife driver 142. As a result, the knife driver 142 and the staple driver 144 are again advanced simultaneously to complete the formation of the staples 65 against the anvil 100. The force required to actuate the staple driver assembly is reduced because the formation of the staples 65 occurs after the tissue is cut.

When the staple actuating lever 92 is returned to its initial position, the main driver 140 (FIG. 17) is moved in the proximal direction by the compression spring 152. As the main driver 140 is retracted, the lugs 164 on the finger extensions 162 engage the annular lip 172 to retract the knife driver 142 and return the annular flange 168 into engagement with the rear wall 124 of the casing 104. By the retraction of the knife driver 142, the annular knife 132 is withdrawn from the backup washer 134. On the other hand, the staple driver 144 is not retracted and remains in its advanced position. This action prevents the staple pusher bars 130 from being withdrawn into the staple holder 102 and avoids the tendency of the tissue to be pinched between the staple pusher bars 130 and the staple holder 102.

As shown in FIGS. 19 and 21, a tubular coupling sleeve 330 extends longitudinally through an opening in the distal end of the actuator handle 90 and is coupled to the proximal end of the flexible shaft assembly 70. The tubular coupling sleeve 330 includes a tubular extension 332 at its distal end into which the flexible shaft assembly 70 is inserted and secured, e.g., by welding. The flexible tubular sheath 75 on the flexible shaft assembly 70 is stretched over the tubular extension at the distal end of the tubular sleeve 330. At the proximal end of tubular sleeve 330 is an annular flange 334 which is urged into engagement with an annular ledge 336 on the actuator handle 90 by a compression spring 338. The flange 334 includes a rearwardly projecting finger 340 which extends into a corresponding groove 342 formed in the handle 90 to preclude any rotation of the shaft assembly 70 about its axis relative to the actuator handle assembly 80.

The tubular coupling sleeve 330 is slidable longitudinally relative to the handle 90 to compensate for differences in deflection of the compression cable 82 and the tension-torsion cable 84 relative to the flexible support shaft assembly 70. Normally, the compression spring 338 biases the annular flange 334 of the tubular coupling sleeve 330 against the annular ledge 336 on the handle 90. The tubular copling sleeve 330 is slidable distally against the bias of the compensating spring 358 to allow the support shaft assembly 70 to move distally relative to the handle 90 to compensate for changes in length of the compression cable 82 and the tension-torsion cable 84 when the stapling head assembly 60 is actuated.

Referring to FIG. 21, the control lever 98 is pivotally mounted on the handle 90 by a pivot pin 352 extending transversely between opposite sides of a mounting block 354. The control lever 98 is located between a front wall 356 and a rear wall 358 of the mounting block 354 and protrudes upwardly through an opening 360 formed in the handle 90. A set screw 362 extends through a threaded opening in the rear wall 358 of the mounting block 354 for engagement with a series of serrated teeth 364 on the control lever 98.

As shown in FIG. 21, the control lever 98 has an upper cutaway section 366 and a lower cutaway section 368 which define a rocker arm 370 provided with a hole for receiving the pivot pin 352. A first, elongated actuator cable 372 is secured to the top of the arm 370 and a second, elongated actuator cable 374 is secured to the bottom of the arm 370. A clamping bolt 376 and nut 378 are provided to fasten the cables 372 and 374 to the arm 370. The actuator cables 372 and 376 are received in longitudinal passages 380 and 382, respectively, formed in the front wall 356 of the mounting block 354. The cables 372 and 374 extend downwardly on opposite sides of the control rod 260 and through an opening 384 formed in the staple actuating lever 92. The cables 372 and 374 pass between the compression member 310 and the coupling sleeve 330 and extend into the flexible support shaft assembly 70.

Referring to FIG. 6, the cables 372 and 374 extend along the flexible shaft assembly 70 through the head joint 62 and terminate at the stapling head assembly 60. The cable 372 is fastened to the top of the hemi-spherical flange 120 and the cable 374 is fastened to the bottom of the hemi-spherical flange 120. As shown in FIG. 8, the cable 372 has an enlarged ball 386 at its distal end which is anchored in a corresponding slot 388 formed at the top of the flange 120. Similarly, the cable 374 has an enlarged ball 390 at its distal end which is anchored in a corresponding slot 392 formed at the bottom of the flange 120.

Referring to FIG. 27, when the control lever 98 is pivoted backward, the cable 372 is pulled proximally while the cable 374 is pushed distally. The tension and compression forces exerted on the cables 372 and 374 are transmitted to the hemi-spherical flange 120 (FIG. 8) of the stapling head assembly 60. As a result, the stapling head assembly 60 is pivoted upward relative to the longitudinal axis or centerline of the flexible shaft assembly 70. When the control lever 98 is pivoted forwardly, the action of the cables 372 and 374 is reversed, i.e., the cable 372 is pushed distally and the cable 374 is pulled proximally. As a result, the stapling head assembly 60 is pivoted downward relative to the longitudinal axis or centerline of the flexible shaft assembly 70.

As shown in FIG. 8, an articulated pivot connection is provided for coupling the tubular firing cable 82 to the driver assembly of the stapling head assembly 60. The articulated pivot connection is achieved by the hollow ball joint coupling member 86 which is pivotally connected by the semi-spherical flanges 88 at its opposite ends to the ferrule 85 and to the main driver 140. The tension-torsion cable 84 extends longitudinally through the ball joint coupling member 86. When the stapling head assembly 60 is pivoted, the ball joint coupling member 86 is capable of pivotal motion at both of its ends by virtue of the semi-spherical flanges 88. The dual pivoting action of the ball joint coupling member 86 permits the tension-torsion coupling 84 to bend gradually through the articulated pivot connection to minimize friction and avoid kinking of the cable 84. The ball joint coupling member 86 facilitates the transmission of compressive forces from the tubular firing cable 82 through the articulated pivot connection to the main driver 140 of the stapling head assembly 160.

The surgical stapling instrument 50 can be used to perform an intraluminal anastomosis in which two sections of tissue are attached together by an array of staples. By way of example, a procedure for joining a pair of hollow organ sections end to end with a plurality of surgical staples arranged in a circular array around a hollow lumen between the organ sections is described. In preparation for the anastomosis, purse string sutures are placed in the hollow organs to be anastomosed. For example, as shown in FIG. 7, two tubular tissue sections 52 and 54 are prepared by threading purse string sutures 56 and 58, respectively, into the tissue in purse string fashion adjacent to the open ends of the tubular tissue sections 52 and 54.

If the surgical procedure is performed using a double purse string suturing technique, the stapling instrument 50 is inserted into the first tubular tissue section 52, e.g., by insertion into the anal opening of the patient, with the anvil assembly 100 attached to the stapling head assembly 60 and completely closed. Prior to the insertion of the stapling instrument 50 into the patient, the thumb wheel 94 and the adjusting knob 96 are rotated to retract the trocar 200 into the guide tube 112 and to clamp the anvil 105 against the staple holder 102. The stapling head assembly 60 is positioned adjacent to the purse stringed end of the tubular tissue section 52.

Next, the thumb wheel 94 is rotated clockwise, as viewed in FIG. 19, to advance the control rod 260 and the tension-torsion cable 84 until the trocar 200 is fully advanced to move the anvil 105 to its open position (FIG. 7). The pivot arms 242 also pivot clockwise to lift the drive gears 248 out of engagement with the peripheral teeth 233 of the Geneva gear wheels 232 and to move the latching fingers 245 downward in front of the cam follower 236. The clockwise rotation of the thumb wheel 94 is converted by the drive gears 248 and the pinion gears 250 into clockwise rotation of the Geneva gear wheels 232.

Figure 26:
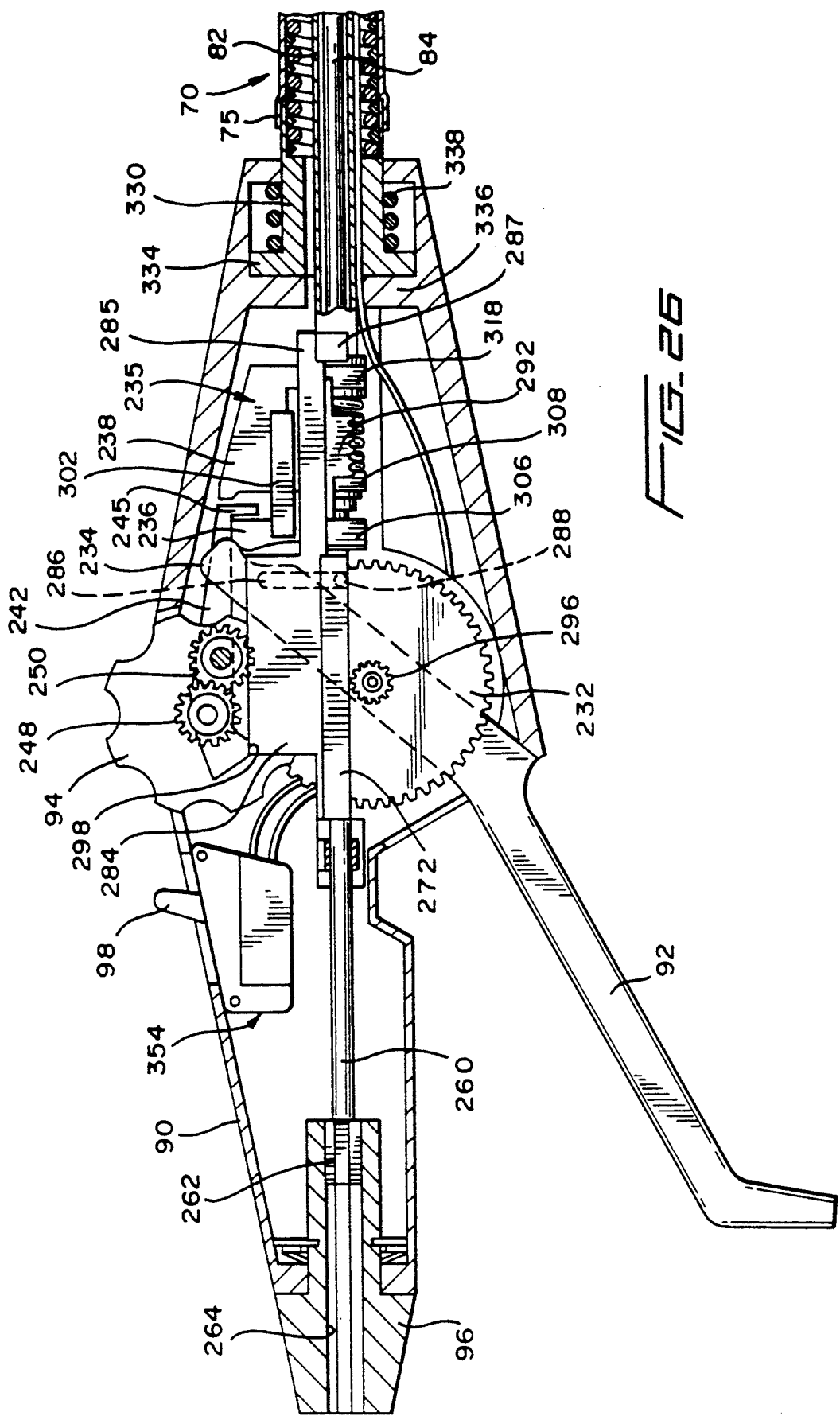
FIG. 26 is a longitudinal section view of the actuator handle assembly illustrating the anvil advancing mechanism fully advanced.

Initially, as shown in FIG. 25, the clockwise rotation of the Geneva gear wheels 232 is translated by the rack and pinion mechanisms 290 into longitudinal movement of the slide members 272 to gradually advance the control rod 260 along the handle 90. Subsequently, as shown in FIG. 26, the clockwise rotation of the Geneva gear wheels 232 is transmitted via the drive pins 288 and the vertical slots 286 in the flanges 284 into longitudinal movement of the slide members 272 to rapidly advance the control rod 260 along the handle 90. The motion of the control rod 260 is transmitted via the tension-torsion cable 84 to the stapling head assembly 60 to move the anvil 105 to its open position away from the staple holder 102.

With the anvil 105 fully advanced, the purse stringed end of the tubular tissue section 52 is drawn together about the cylindrical trocar body 202 by pulling and tightening the purse string suture 56. After the purse stringed tissue is drawn against the cylindrical trocar body 202, the purse string suture 56 is tied to hold the tissue against the trocar body 202.

Next, the anvil 105 is inserted into the purse stringed end of the tubular tissue section 54 and the tissue is drawn together about the anvil shaft 110 by pulling and tightening the purse string suture 58. Preferably, the purse stringed tissue is pulled against the anvil shaft 110 in the tying notch 117 distally of the splines or keys 111 and the purse stringed suture 58 is tied together. If desired, the anvil shaft 110 may be detached from the trocar 200 to facilitate the insertion of the anvil 105 into the tubular tissue section 54. After the purse stringed end of the tubular tissue section 54 is tied against the anvil shaft 110 by the purse stringed suture 58, the anvil assembly 100 is re-attached to the trocar 200.

After the purse stringed ends of the tubular tissue sections 52 and 54 are tied, the thumb wheel 94 is rotated counterclockwise, as viewed in FIG. 26, to retract the trocar 200 into the guide tube 112 to move the anvil 105 toward the staple holder 102. Initially, the anvil 105 and the trocar 200 are rapidly retracted into the guide tube 112 as the control rod 260 is rapidly retracted by the action of the drive pins 288 in the vertical slots 286 of the flanges 284 to retract the slide members 272. Subsequently, the anvil assembly 100 and the trocar 200 are gradually retracted into the guide tube 112 as the control rod 260 is retracted by engagement of the racks 292 with the pinion gears 296 to clamp the tissue between the anvil 105 and the staple holder 102.

As the trocar 200 is retracted, the trocar body 202 slides through the purse stringed end of the tissue section 52 to pull the anvil shaft 110 through the purse stringed tissue into the guide tube 112. The chamfered edges 129 (FIG. 28) of the anvil splines 111 and the chamfered edges 229 (FIG. 31) of the trocar splines 212 facilitate the passage of the purse stringed tissue across the transition point between the trocar body 202 and the anvil shaft 110.

When the anvil shaft 110 enters the guide tube 112, the external splines or keys 111 (FIG. 34) on the anvil shaft 110 are received and guided between the internal splines or keys 113 (FIG. 33) of the guide tube 112 to circumferentially align the anvil 105 with the staple holder 102. The distal end of the guide tube 112 pushes the purse stringed tissue over the transition between the trocar 200 and the anvil shaft 110 and over the external splines 111. As a result, the staple forming grooves 108 (FIG. 34) on the anvil 105 are precisely aligned with the staple forming slots 106 (FIG. 33) of the staple holder 102.

After the tissue is clamped between the anvil 105 and the staple holder 102, the adjusting knob 96 is rotated to set the gap between the anvil 105 and the staple holder 102 to produce a desired staple height. The stapling instrument 50 is fired by grasping and pivoting the staple actuating lever 92 clockwise, as viewed in FIG. 27, to move the staple actuating lever 92 to its operative position. As a result, the cam 234 on the staple actuating lever 92 is pivoted clockwise to drive the cam follower assembly 235 in the distal direction to advance the actuator sleeve 310 and the firing cable 82 longitudinally along the shaft assembly 70. The motion of the actuator sleeve 310 is transmitted via the firing cable 82 to the stapling head assembly 60 to staple and cut the tissue.

The cam follower assembly 235 is operable in two stages. In the first stage of operation, the cam 234 slides downward along the inclined cam surface 246 and the cam follower assembly 235 is rapidly advanced with a high mechanical advantage to rapidly advance the main driver 140, the knife driver 142 and the staple driver 144 in the stapling head assembly 60 until each staple 65 (FIG. 36) penetrates into the tissue and engages the anvil 105. In the second stage of operation, the cam 234 slides downwardly along the concave cam surface 248 and advances the cam follower assembly 235 with a low mechanical advantage to transmit a high compressive force via the firing cable 82 to actuate the stapling head assembly 60 to cut the tissue and complete the formation of each staple 65 (FIG. 37).

Figure 16:
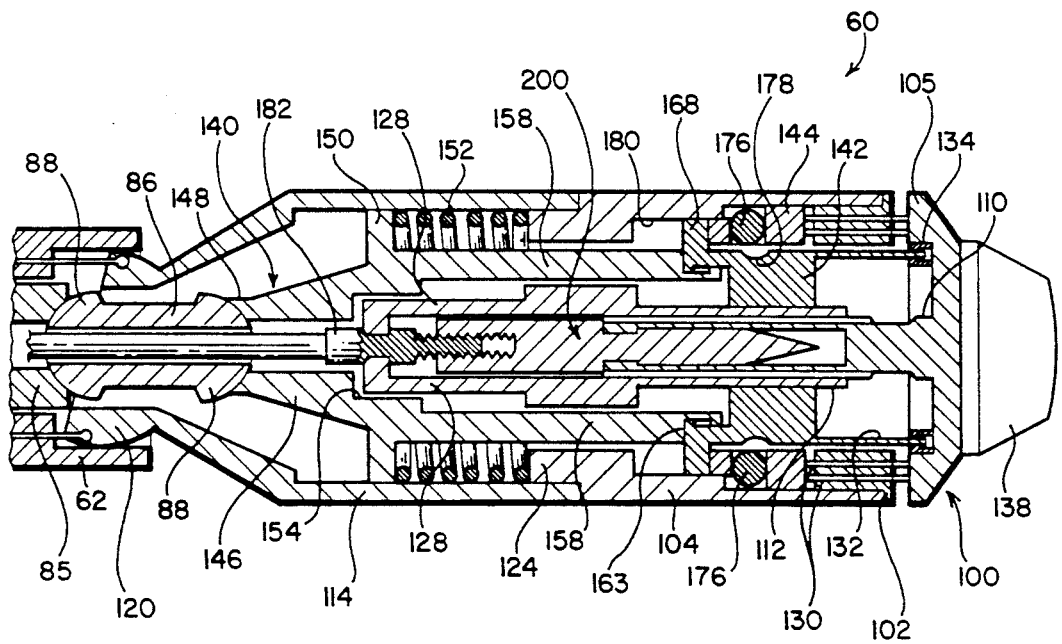
FIG. 16 is an enlarged longitudinal section view illustrating a final stage of the operation of the stapling head assembly.

The stapling head assembly 60 also operates in multiple stages. First, the main driver 140, the knife driver 142 and the staple driver 144 are advanced simultaneously until each staple 65 (FIG. 36) penetrates into the tissue and engages the anvil 105. Second, the staple driver 144 is disengaged from the knife driver 142 while the main driver 140 continues to advance the knife driver 142. The annular knife 132 is advanced by the knife driver 142 to cut the tissue against the backup washer 134. As shown in FIG. 16, the annular knife 132 slits the backup washer 134 into two annular sections. Third, after the tissue is cut, the staple driver 144 is re-engaged by the knife driver 142 and again advanced by the main driver 140 to complete the formation of each staple 65 against the anvil 105. Each of the staples 65 (FIG. 37) is formed into a B-shaped configuration to staple the tissue sections 52 and 54 together.

Figure 17:
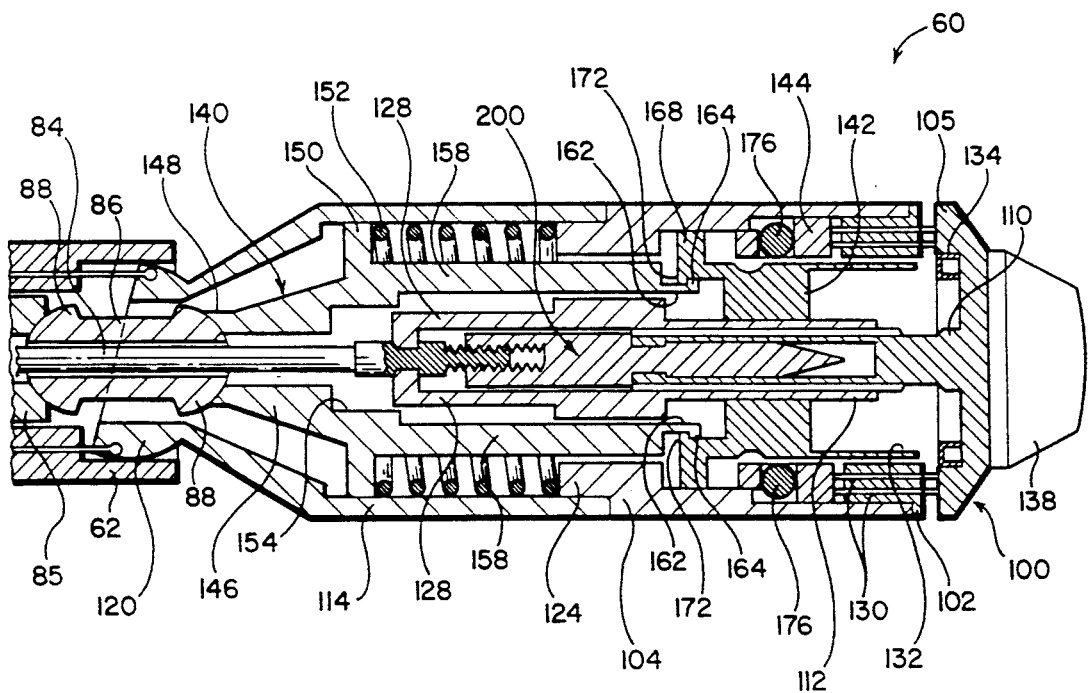
FIG. 17 is an enlarged longitudinal section view illustrating the stapling head assembly after the stapling and cutting operation is completed.

After the stapling and cutting of the tissue is completed, the staple actuating lever 92 is released and returned to its inoperative position by the compression spring 324 of the cam follower assembly 235 and the compression spring 152 of the stapling head assembly 60. The compression spring 152 returns the main driver 140 to its retracted position. As the main driver 140 is retracted, the lugs 164 on the finger extensions 162 engage the annular lip 170 of the knife driver 142. As shown in FIG. 17, the knife driver 142 is partially retracted and the annular knife 132 is withdrawn from the backup washer 135. However, the knife driver 144 remains in its advanced position to prevent the staple pusher bars 130 from retracting into the staple holder 102.

Next, the stapled tissue between the anvil 105 and the staple holder 102 is released by rotating the thumb wheel 94 clockwise to advance the anvil assembly 100 away from the stapling head assembly 60. The anvil 105 is moved through the lumen by manipulating the staple tissue in a suitable manner to slip the anvil 105 through the stapled lumen. Then, the stapling instrument 50 is withdrawn from the patient removing the severed donut-shaped piece of tissue on the anvil shaft 110 and leaving behind the stapled lumen between the tubular tissue sections 52 and 54.

Referring to FIG. 27, the tubular coupling sleeve 330 and the compression spring 338 provide compensation for changes in length of the firing cable 82 and the tension-torsion cable 84 relative to the flexible support shaft assembly 70. When the stapling instrument 50 is fired by moving the staple actuating lever 92 to its operative position, the firing cable 82 is placed in compression and the tension-torsion cable 84 is placed in tension. Thus, there is a tendency for the tension-torsion cable 84 to stretch in length when the stapling instrument 50 is fired. The tubular coupling sleeve 330 allows the flexible shaft assembly 70 to move distally relative to the actuator handle assembly 80 to compensate for changes in length of the tension-torsion cable 84 when the stapling instrument 50 is actuated.

The actuator handle assembly 80 of the stapling instrument 50 is ergonomically designed to facilitate the application and transmission of the required operating forces to the stapling head assembly 60. The staple actuating lever 92 actuates the cam follower assembly 235 which is operable in two stages to actuate the driver assembly in the stapling head assembly 60. In the first stage of operation, the cam follower assembly 235 is rapidly advanced with a low mechanical advantage by the staple actuating lever 92 as the cam 234 is moved along the inclined cam surface 246. The staple driver assembly is rapidly advanced to drive the staples 65 from the staple holder 102 into the tissue clamped by the anvil 105. In the second stage of operation, the cam follower assembly 235 is advanced gradually with a high mechanical advantage by the staple actuating lever 92 as the cam 234 is moved along the concave cam surface 246. The driver assembly is gradually advanced to cut the tissue and form the staples 65 against the anvil 105.

In the first stage of operation, when the actuator handle assembly 80 is grasped with an open hand by a surgeon, only a small manual operating force is needed to pivot the staple actuating lever 92 toward the actuator handle 90 to actuate the cam follower assembly 235 and the main driver 140 to advance the staples 65 into the tissue. As the staple actuating lever 92 is pivoted toward the actuator handle 90, the hand of the surgeon closes to a position in which a higher manual operating force can be applied to the staple actuating lever 92 for advancing the cam follower assembly 235 and the main driver 140 to cut the tissue and form the staples 65 against the anvil 105.

Referring to FIG. 38, an alternative embodiment of the stapling head assembly, generally 400, includes a hollow cylindrical housing 402 provided with a rear hemispherical flange 404 which is pivotally connected to the head joint 62 by a pair of pivot pins 406 (one shown). A front cylindrical casing 408 has a rear offset portion 410 which is reduced in diameter and received by the rear cylindrical housing 402. In the example shown in FIG. 38, the rear cylindrical housing 402 and the front cylindrical casing 408 have an outer diameter of 19 millimeters. The casing 408 includes a rear cylindrical wall 412 provided with a central circular bore 414. A guide tube 416 projects forwardly from the rear cylindrical wall 412 in axial alignment with the circular bore 414. Also, a plurality of locating fingers 418 extends rearwardly from the cylindrical wall 412 in alignment with the circular bore 414. Preferably, a set of four locating fingers 418 (FIG. 39) are spaced apart at equal angular intervals around the circular bore 414. Each locating finger 418 includes an inwardly projecting detent 420 which is received in the circumferential groove 184 formed in the cable coupling member 182.

In the stapling head assembly 400 of FIG. 38, a staple holder 422 is mounted at the front end of the hollow cylindrical casing 408. The staple holder 422 has a plurality of staple receiving slots 424 arranged in two closely spaced concentric annular rows for receiving a plurality of surgical staples 65. An anvil assembly 430 includes a circular anvil 432 secured by a screw 428 to an elongated anvil shaft 434 which is slidably received in the guide tube 416 provided on the casing 408. The proximal end of the anvil shaft 434 is divided into a set of resilient fingers 435 which detachably engage a trocar 426. The trocar 426 is threadably attached to the shank 188 of the cable coupling member 182 and is slidably mounted in the guide tube 416.

As shown in FIG. 41, sixteen staple receiving slots 424 are provided in the staple holder 422 which are arranged in two concentric annular rows with eight slots 424 in each row. On the anvil 432 (FIG. 42), sixteen pairs of staple forming grooves 436 are also arranged in two concentric annular rows in alignment with the staple receiving slots 424 of the staple holder 422. A set of eight internal circumferentially disposed splines or keys 438 is formed on the inside of the guide tube 416 for aligning the anvil 432 with the staple holder 422. The anvil shaft 434 is slidably keyed to the casing 408 by a set of eight longitudinal splines or keys 440 formed on the outer surface of the anvil shaft 434. The anvil splines 440 are received between the splines or keys 438 formed on the inside of the guide tube 416 when the anvil shaft 434 is retracted by the trocar 426 into the central bore 414 of the casing 408. The trocar 426 is slidably keyed to the casing 408 by a set of eight longitudinal splines or keys 442 (FIG. 40) formed on the outer surface of the trocar 426. The trocar splines 442 are received between the internal splines or keys 438 formed on the guide tube 416 when the trocar 426 is retracted into the central bore 414 of the casing 408.

Referring to FIG. 38, the stapling head assembly 400 includes a plurality of staple pusher bars 444 slidably mounted for longitudinal movement in the staple receiving slots 424 of the staple holder 422. The stapling head assembly 400 also contains an annular tissue cutting knife 446 which is concentric with and located inside the annular array of staples 65 in the staple holder 422. The anvil assembly 430 supports an annular backup washer 448 of channel-shaped cross section against which the tissue is cut by the knife 446.

The stapling head assembly 400 includes a driver assembly comprising a main driver 450, a knife driver 452 and a staple driver 454 which are slidably mounted for longitudinal movement within the casing 408. The main driver 450 includes a conically tapered rear portion 456 which pivotally engages the front hemispherical flange 88 of the ball joint coupling member 86. A compression spring 458 is interposed between an annular flange 460 of the main driver 450 and the cylindrical wall 412 of the casing 408 to bias the main driver 450 rearwardly relative to the casing 408. The tension-torsion cable 84 extends through an axial bore 462 and a counterbore 464 formed in the conically tapered portion 456 of the main driver 450. The counterbore 464 is sufficiently large in diameter to receive the proximal ends of the locating fingers 418 when the stapling head assembly 400 is ready to be fired. An annular ledge 466 is provided at the front edge of the counterbore 464 for engaging the proximal ends of the locating fingers 418 to prevent firing of the main driver 450 when the locating fingers 418 are flexed apart.

Referring to FIG. 38, the main driver 450 includes a plurality of elongated fingers 468 which slidably extend through a set of circular openings 470 provided in the rear cylindrical wall 412 of the casing 408. In the preferred embodiment, a set of four driver fingers 468 is provided on the main driver 450 which are received in four openings 470 spaced at equal angular intervals on the casing 408. A narrow extension 472 projects forwardly from the front edge of each driver finger 468. A lug 474 projects radially outward at the front of each extension 472.

The knife driver 452 consists of an annular body provided with an axial bore 476 which slidably receives the guide tube 416 and allows the knife driver 452 to slide along the guide tube 416 relative to the casing 408. The annular knife 446 is secured, e.g., by swedging, to a front annular flange 478 on the knife driver 142. An annular flange 480 at the rear of the knife driver 452 defines a counterbore 482 for receiving the finger extensions 472. The driver fingers 468 have front edges 484 which engage the rear surface of the flange 480 when the main driver 450 is advanced. An annular lip 486 projecting radially inward from the flange 480 is engaged by the lugs 474 on the finger extensions 472 to move the knife driver 452 rearwardly when the main driver 140 is retracted. An intermediate flange 488 projects radially outward from the knife driver 452 and engages an annular ledge 490 on the casing 408 when the stapling head assembly 400 is ready to be fired.

The staple driver 454 is annular in shape and provided with a series of circumferentially spaced sockets 492 for receiving a plurality of balls 494. Preferably, a set of eight balls 494 is received in a set of eight sockets 492 which are spaced at equal angular intervals on the staple driver 454. The knife driver 452 is generally cylindrical in shape and is slidably received within the annular staple driver 454. The knife driver 452 includes a circumferential groove 496 formed in its outer surface for receiving the balls 494. The balls 494 are initially held in the circumferential groove 496 by an inner cylindrical wall 498 of the casing 408 so that the knife driver 452 and the staple driver 454 are coupled together by the balls 494 for simultaneous advancement by the main driver 450. The staple driver 454 engages the staple pusher bars 444 which extend into the staple receiving slots 424 to drive the staples 65 from the staple holder 422 when the staple driver 454 is advanced.

The operation of the stapling head assembly 400 is substantially the same as the operation of the stapling head assembly 60 described above. To open the stapling head assembly 400, the thumb wheel 94 (FIG. 25) is actuated to advance the tension-torsion cable 84 which, in turn, advances the cable coupling member 182, the trocar 426 and the anvil assembly 430 (FIG. 38). When the cable coupling member 182 is advanced to move the anvil assembly 430 to its open position, the locating fingers 418 are flexed apart to engage the annular ledge 466 and prevent the main driver 450 from being advanced. When the tension-torsion cable 84 is retracted to move the anvil assembly 430 to its closed position, the detents 420 of the locating fingers 418 snap into the annular groove 184 to capture and support the cable coupling member 182 for axial rotation.

To adjust the anvil gap, the adjusting knob 96 (FIG. 25) is rotated to transmit rotation via the tension-torsion cable 84 to the cable coupling member 182 (FIG. 38). The rotation of the cable coupling member 182 is translated by the threaded shank 188 into longitudinal movement of the trocar 426 which is slidably keyed to the guide tube 416. The longitudinal movement of the trocar 426 is transmitted to the anvil shaft 434 to adjust the gap between the anvil 432 and the staple holder 422 to select the staple height to be produced.

When the staple actuating lever 92 (FIG. 27) is actuated, a compression force is applied via the firing cable 82, the ferrule 85 and the ball joint coupling member 86 to advance the main driver 450 (FIG. 38). The locating fingers 418 are received in the counterbore 464 of the main driver 450 and are latched against the cable coupling member 182 so that the tension applied to the tension-torsion cable 84 is transmitted to the casing 408 and to the anvil 432. Initially, the knife driver 452 and the staple driver 454 are coupled together by the balls 494 and are advanced simultaneously to drive the staples 65 from the staple holder 422 into the tissue. When the balls 494 are freed from the wall 498, the staple driver 454 is disengaged from the knife driver 452. As a result, the staple driver 454 remains stationary while the knife driver 452 advances the annular knife 446 to cut through the tissue and into the backup washer 448 on the anvil 432. Subsequently, the staple driver 454 is reengaged by the annular flange 488 on the knife driver 452 which advances the staple driver 454 to complete the formation of the staples 65 against the anvil 432. As explained above, the force required to actuate the staple driver assembly is reduced because the formation of the staples 65 occurs after the tissue is cut.

Finally, when the staple actuating lever 92 (FIG. 21) is returned to its initial position, the main driver 450 (FIG. 38) is moved in the proximal direction by the compression spring 458. As the main driver 450 is retracted, the lugs 474 on the finger extensions 472 engage the annular lip 486 to retract the knife driver 452 and return the annular flange 488 into engagement with the annular ledge 490 on the casing 408. The annular knife 446 is withdrawn from the backup washer 448, while the staple driver 454 is not retracted and remains in its advanced position. A severed donut-shaped piece of tissue (not shown) remains on the anvil shaft 434 and is removed after the stapling head assembly 400 is withdrawn from the patient.

The invention in its broader aspects is not limited to the specific details of the preferred embodiments shown and described, and those skilled in the art will recognize that the invention can be practiced with modification within the spirit and scope of the appended claims.

We claim:

1. A surgical stapling instrument for applying a plurality of surgical staples to tissue, comprising:

a stapling head assembly including a staple holder for receiving a plurality of surgical staples, an anvil for clamping the tissue against said staple holder and a staple driver for engaging and driving the staples from said staple holder into the tissue and against said anvil;

an actuator handle assembly including anvil control means for moving said anvil relative to said staple holder;

a shaft assembly including a longitudinal support shaft with a distal end for mounting said stapling head assembly and a proximal end connected to said actuator handle assembly; and wherein said anvil control means comprises:

a thumb wheel rotatably mounted on said actuator handle assembly;

a gear wheel on said actuator handle assembly mounted for rotation by said thumb wheel;

a slide mechanism connected to said anvil and slidably mounted for longitudinal movement along said actuator handle assembly;

said gear wheel coupled to said slide mechanism by a first coupling over a first stage of operation of said anvil control means in which tissue is not clamped against the staple holder by the anvil; and said gear wheel coupled to said slide mechanism by a second coupling over a second stage of operation of said anvil control means in which tissue is clamped against the staple holder by the anvil.

2. The stapling instrument of claim 1, wherein:

said first coupling comprises a drive pin on said gear wheel received by a slot in said slide mechanism for converting rotation of said gear wheel into longitudinal movement of said slide mechanism.

3. The stapling instrument of claim 1, wherein:

said second coupling comprises a rack on said slide mechanism and a pinion gear coupled to said gear wheel for converting rotation of said gear wheel into longitudinal movement of said slide mechanism.

4. The stapling instrument of claim 1, wherein:

said stapling head assembly is pivotable about said support shaft distal end.

5. A surgical stapling instrument for applying one or more surgical staples to tissue, comprising:

a stapling head assembly including a staple holder for receiving one or more surgical staples, an anvil for clamping the tissue against said staple holder, and a staple driver for engaging and driving the staples from said staple holder into the tissue and against said anvil;

an actuator handle assembly including staple actuator means for actuating said staple driver;

a shaft assembly including a longitudinal support shaft with a distal end for mounting said stapling head assembly and a proximal end connected to said actuator handle assembly; and wherein said staple actuator means includes:

a staple actuating lever pivotally mounted on said actuator handle assembly;

a cam mounted on said staple actuating lever;

a cam follower coupled to said staple driver and slidably mounted for longitudinal movement along said actuator handle assembly; and said cam follower including a first cam surface engaged by said cam for actuating said staple driver over a first stage of operation in which said staples are driven through tissue and against said anvil, and a second cam surface engaged by said cam for actuating said staple driver over a second stage of operation in which said staples are formed in the tissue by compression against said anvil.

6. A surgical stapling instrument for applying a plurality of surgical staples to tissue, comprising:

a stapling head assembly including a staple holder for receiving a plurality of surgical staples, an anvil for clamping the tissue against said staple holder, and a staple driver for engaging and driving the staples from said staple holder into the tissue and against said anvil;

an actuator handle assembly including staple actuator means for advancing said staple driver relative to said staple holder;

a shaft assembly including a longitudinal support shaft with a distal end for mounting said stapling head assembly and a proximal end connected to said actuator handle assembly;

a tension member contained within said support shaft and connected to said actuator handle assembly at a proximal end, and to said stapling head assembly at a distal end, said tension member transmitting tension from said actuator handle assembly to said anvil to resist the forces exerted on said anvil when the staples are formed;

a compression member contained within said support shaft and connected to said actuator handle assembly at a proximal end, and to said stapling head assembly at a distal end, said compression member transmitting a compressive force from said staple actuator means to advance said staple driver to drive the staples from said staple holder into the tissue and to form the staples against said anvil; and wherein said staple actuator means includes:

a staple actuating lever pivotally mounted on said actuator handle assembly;

a cam mounted on said staple actuating lever;

a cam follower coupled to said staple driver and slidably mounted for longitudinal movement along said actuator handle assembly; and said cam follower including a first cam surface engaged by said cam for actuating said staple driver over a first stage of operation in which said staples are driven through tissue and against said anvil and a second cam surface engaged by said cam for actuating said staple driver over a second stage of operation in which said staples are formed in the tissue by compression against said anvil.

7. A surgical stapling instrument for applying a plurality of surgical staples to tissue, comprising:

a stapling head assembly including a staple holder for receiving a plurality of surgical staples, an anvil for clamping the tissue against said staple holder, and a staple driver for engaging and driving the staples from said staple holder into the tissue and against said anvil;

an actuator handle assembly including anvil control means for moving said anvil relative to said staple holder;

a shaft assembly including a longitudinal support shaft with a distal end for mounting said stapling head assembly and a proximal end connected to said actuator handle assembly; and wherein said anvil control means comprises:

a thumb wheel rotatably mounted on said actuator handle assembly;

a gear wheel on said actuator handle assembly mounted for rotation by said thumb wheel;

a slide mechanism connected to said anvil and slidably mounted for longitudinal movement along said actuator handle assembly;

said gear wheel coupled to said slide mechanism by a
first coupling over a first stage of operation of said
anvil control means in which tissue is not clamped
against the staple holder by the anvil; and
said gear wheel coupled to said slide mechanism by a
second coupling over a second stage of operation
of said anvil control means in which tissue becomes
clamped against the staple holder by the anvil;
first pivot means for pivotably connecting said stapling head assembly to said support shaft; and
second pivot means on said actuator handle assembly
controlling said first pivot means.

* * * * *